United States Patent [19]

Boden et al.

[11] Patent Number: 4,465,863

[45] Date of Patent: Aug. 14, 1984

[54] BRANCHED C₁₃-ALK-1-EN-5-ONES, USE THEREOF IN PERFUMERY, PROCESS FOR PREPARING SAME AND INTERMEDIATES USED IN SAID PROCESS

[75] Inventors: Richard M. Boden, Ocean; Steven D. Temes, Hazlet; Theodore J. Tyszkiewicz, Sayreville; Marie R. Hanna, Hazlet, all of N.J.

[73] Assignee: International Flavors & Fragrances Inc., New York, N.Y.

[21] Appl. No.: 441,375

[22] Filed: Nov. 12, 1982

[51] Int. Cl.³ .................................................. C07C 49/203
[52] U.S. Cl. ................................ 568/417; 252/522 R; 252/174.11; 560/174; 562/577; 568/412; 568/388; 568/393; 568/391
[58] Field of Search ....................... 568/417, 388, 397; 260/463; 560/106, 174

[56] References Cited

U.S. PATENT DOCUMENTS

| | | | |
|---|---|---|---|
| 2,834,811 | 5/1958 | Georgieff et al. | 568/388 |
| 3,668,255 | 6/1972 | Neuly et al. | 568/388 |
| 3,943,177 | 3/1976 | Helmlinger et al. | 568/417 |
| 4,031,131 | 6/1977 | Renner et al. | 260/463 |
| 4,031,141 | 6/1977 | Hoffmann et al. | 568/388 |
| 4,117,015 | 9/1978 | Hall et al. | 568/348 |

FOREIGN PATENT DOCUMENTS 55-27135  2/1980  Japan ................................. 568/417

OTHER PUBLICATIONS

Hilgetag et al., "Preparative Org. Chem.", John Wiley & Sons, pp. 1047–1049, 916–917, 1012–1013 (1972).

Primary Examiner—James H. Reamer
Attorney, Agent, or Firm—Arthur L. Liberman

[57] ABSTRACT

Described are compounds defined according to the structure:

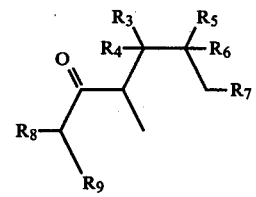

wherein $R_3$, $R_4$, $R_5$, $R_6$ and $R_7$ represent hydrogen or methyl with the provisos that:
  (i) the sum total of carbon atoms in $R_3$, $R_4$, $R_5$, $R_6$ and $R_7$ is three;
  (ii) when $R_7$ is methyl, then $R_5$ and $R_6$ are both methyl, and
  (iii) when either $R_3$ or $R_4$ is methyl, then $R_7$ is hydrogen and wherein $R_8$ represents hydrogen, acetyl, alkoxyacyl, hydroxyacyl, or alkali metal carboxylate; and $R_9$ is hydrogen or allyl with the additional proviso that $R_8$ and $R_9$ are not both hydrogen.

Also described is the use of the subgenus of such compounds defined according to the structure:

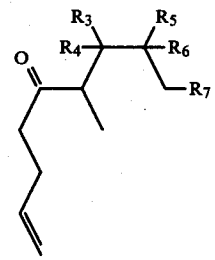

in augmenting or enhancing the aroma of perfume compositions, colognes and perfumed articles including solid or liquid nonionic, cationic, anionic or zwitterionic detergents, fabric softener compositions, fabric softener articles, cosmetic powders, hair preparations and the like.

1 Claim, 22 Drawing Figures

GLC PROFILE FOR EXAMPLE A.

GLC PROFILE FOR EXAMPLE A.

GLC PROFILE FOR EXAMPLE A.

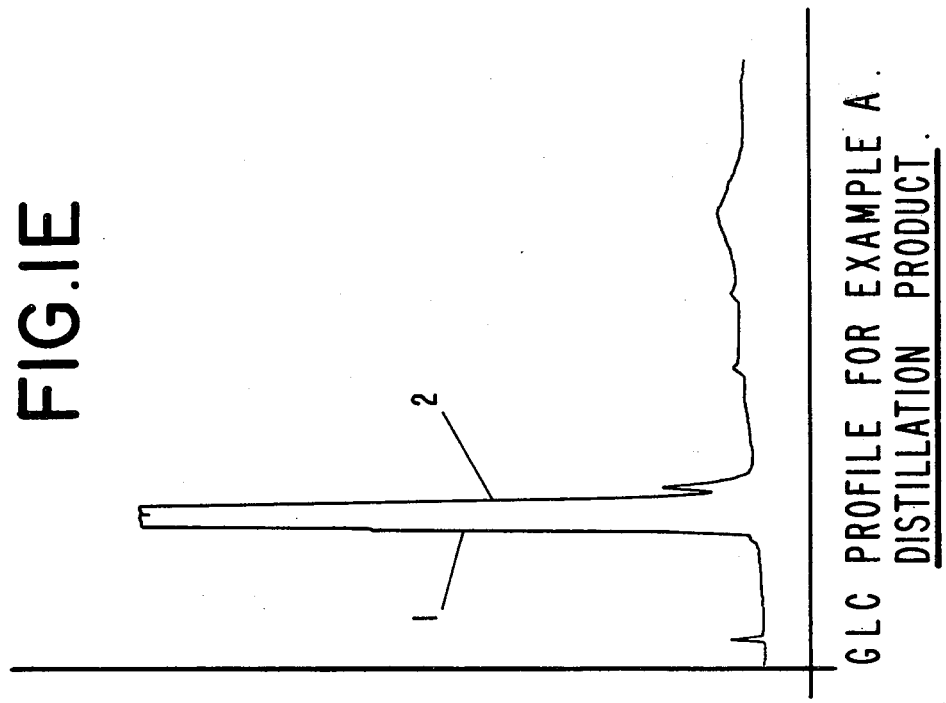
FIG.IE
GLC PROFILE FOR EXAMPLE A. DISTILLATION PRODUCT.
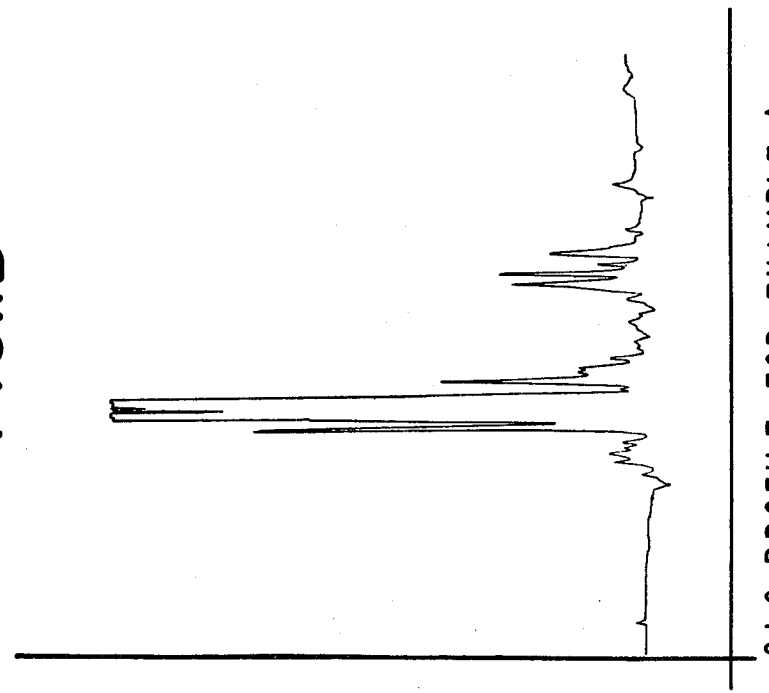
FIG.ID
GLC PROFILE FOR EXAMPLE A. CRUDE PRODUCT.

NMR SPECTRUM FOR PEAK I OF GLC OF FIG.1E

IR SPECTRUM FOR PEAK I, OF GLC OF FIG.1E.

NMR SPECTRUM FOR
PEAK 2, OF GLC OF FIG. 1E

IR SPECTRUM FOR  PEAK 2 OF GLC OF FIG. 1E

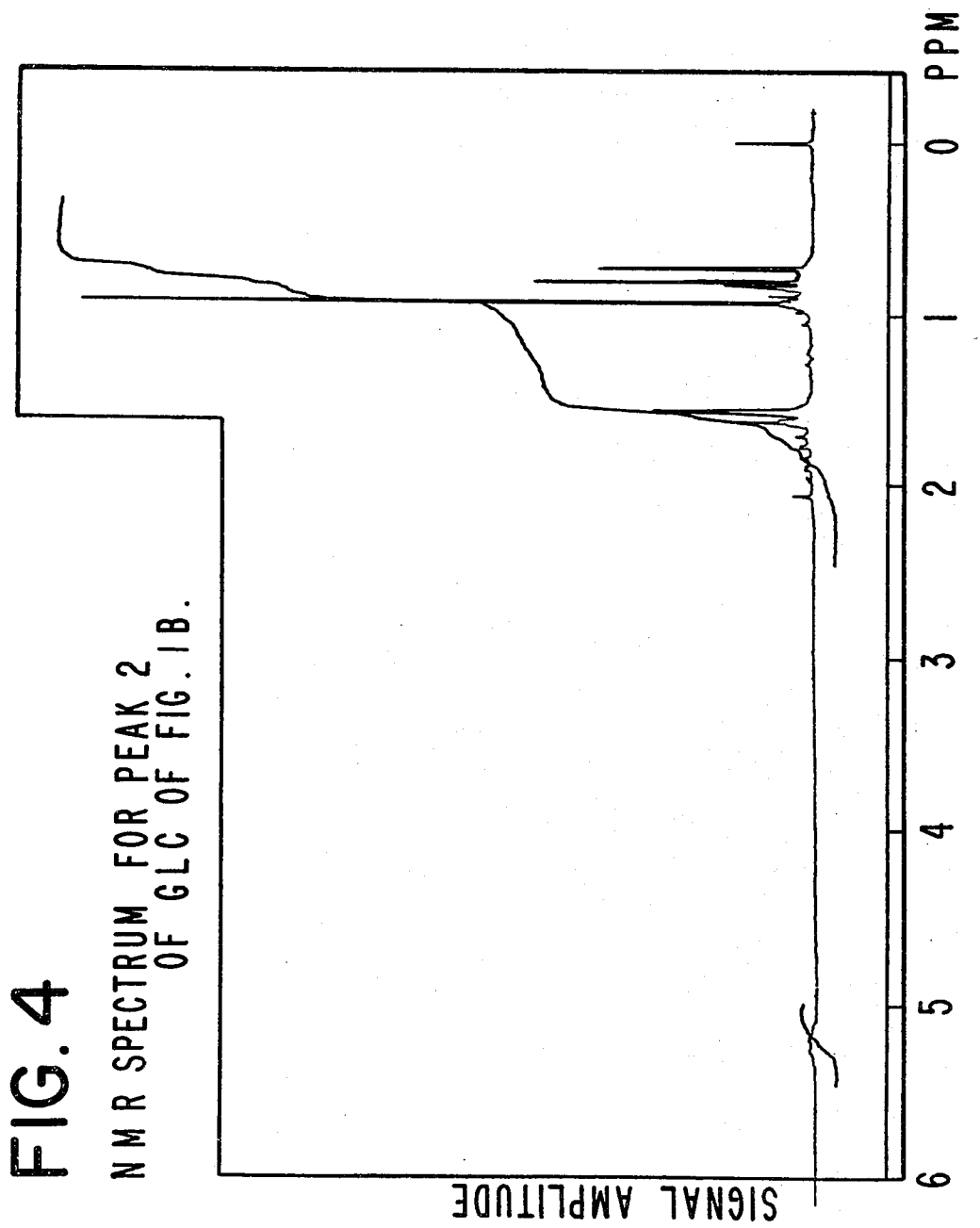

GLC PROFILE FOR EXAMPLE I.

NMR SPECTRUM FOR EXAMPLE I — PEAKS 31, 32 & 33 OF FIG. 5

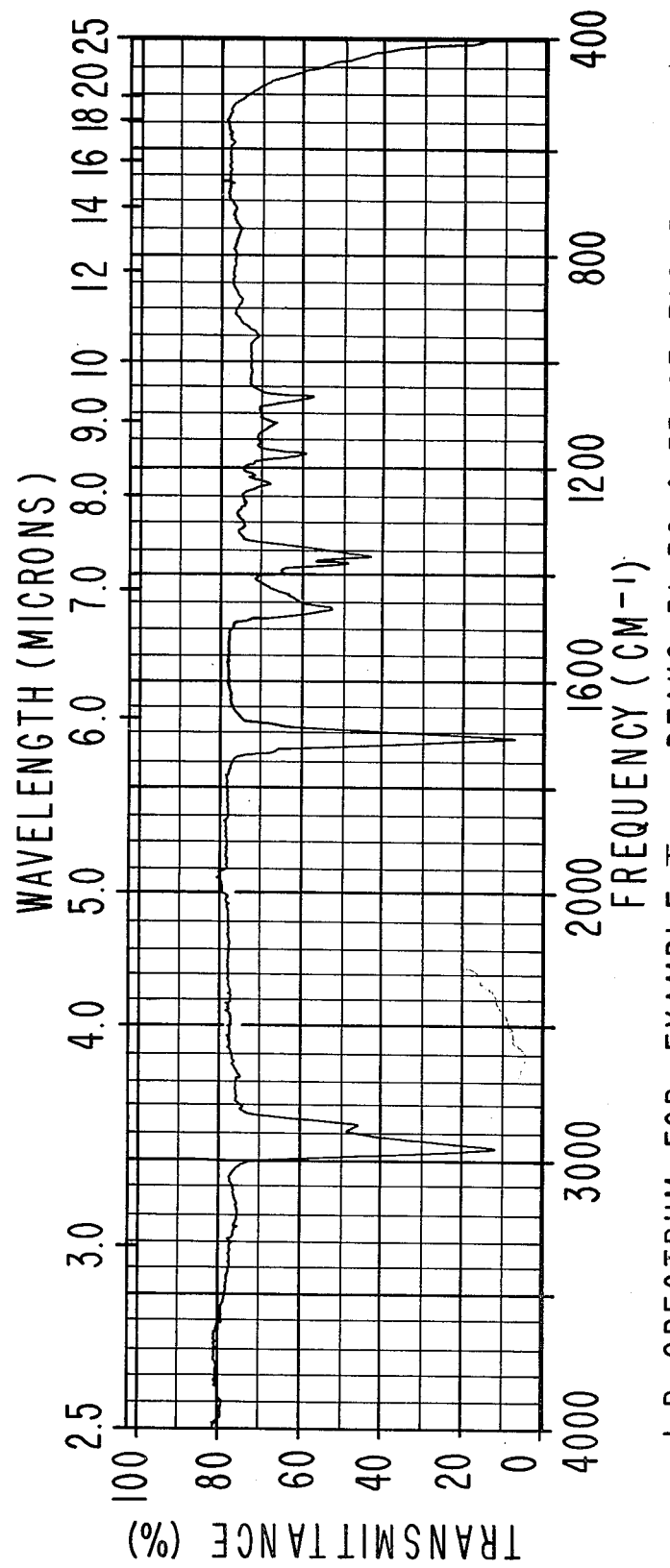

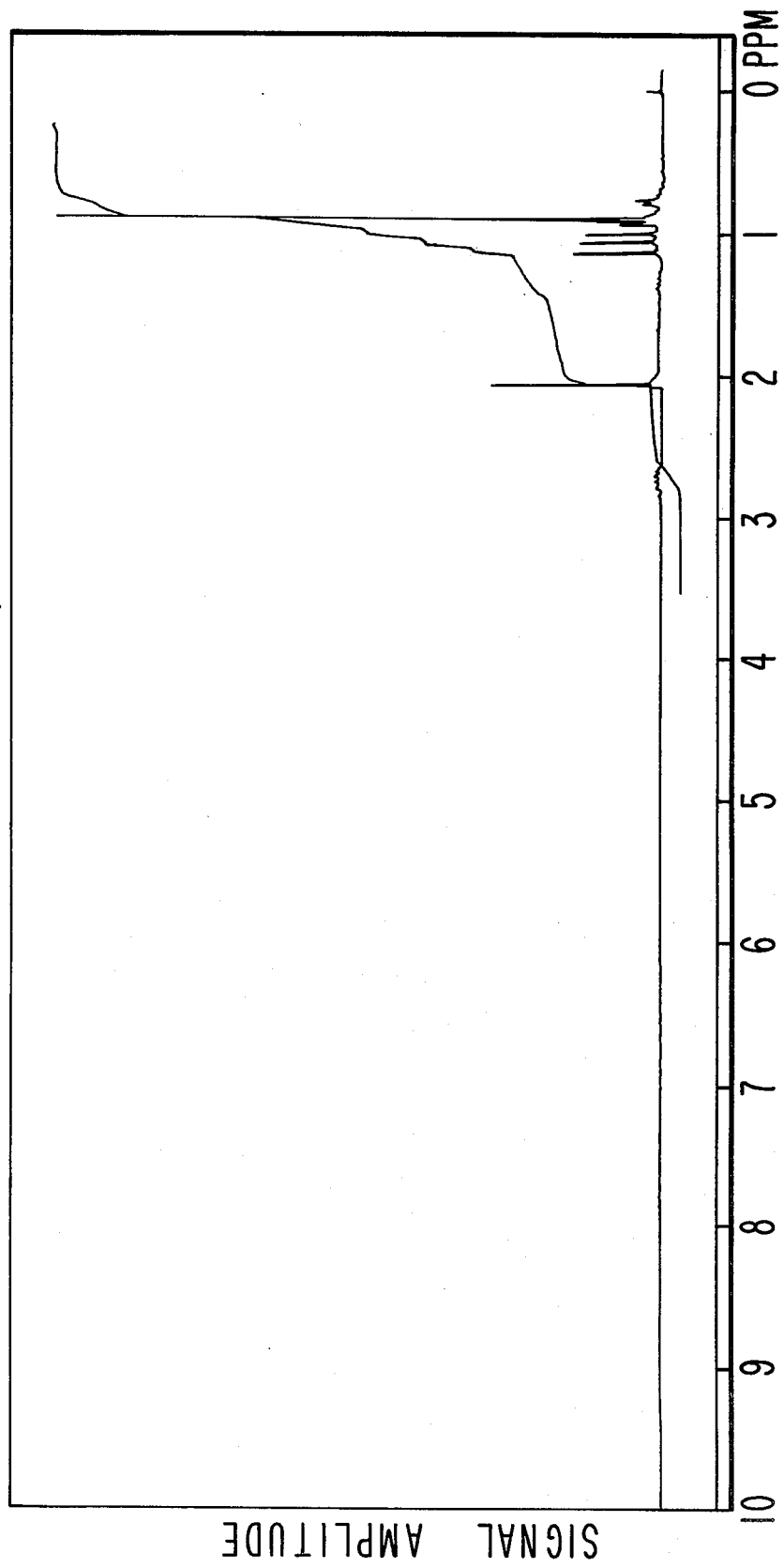
FIG. 8 NMR SPECTRUM FOR EXAMPLE I — PEAKS 21, 22 & 23 OF FIG. 5.

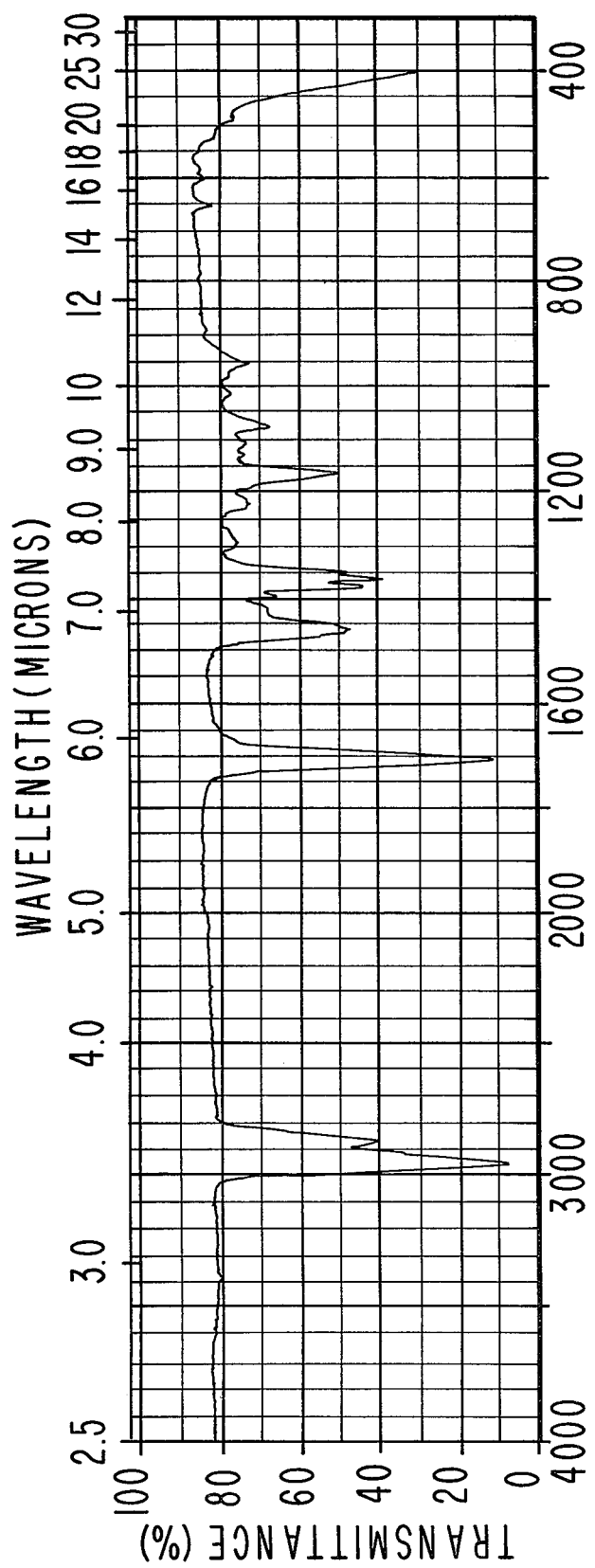

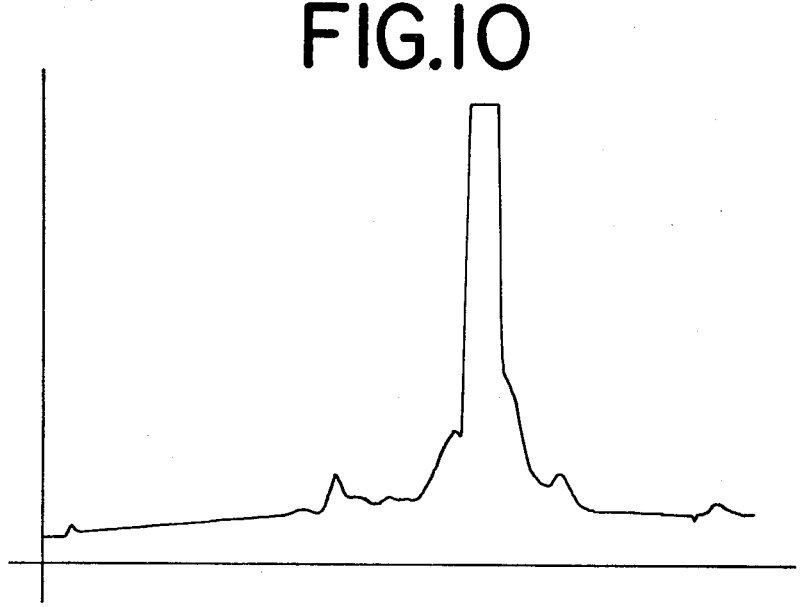
GLC PROFILE FOR FRACTION 5 OF EXAMPLE II.
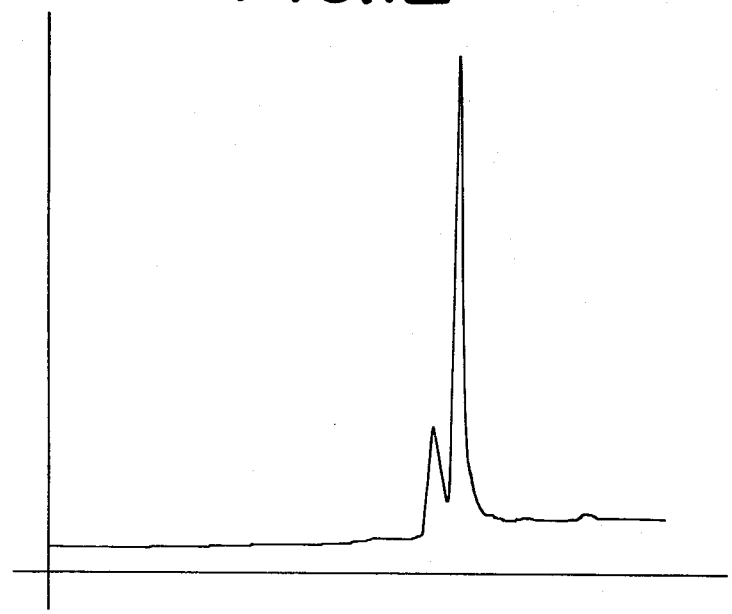
GLC PROFILE FOR FRACTION 7 OF EXAMPLE II.

GLC PROFILE FOR FRACTION 6 OF EXAMPLE II.

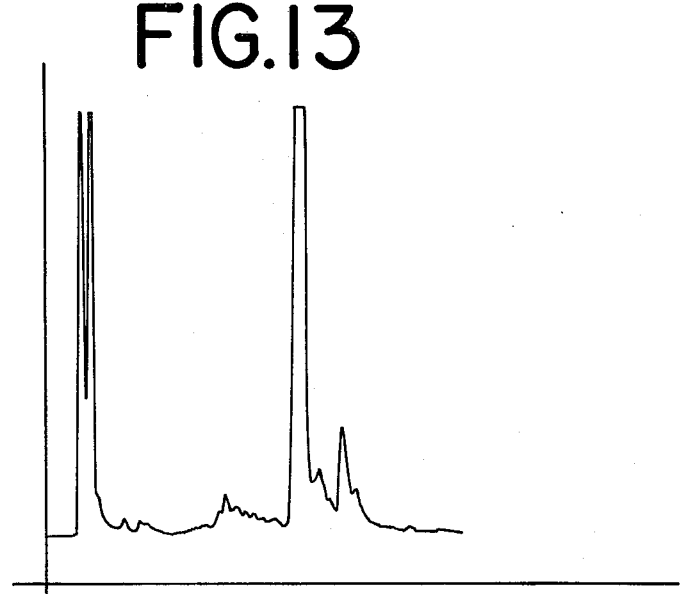
GLC PROFILE FOR EXAMPLE III.
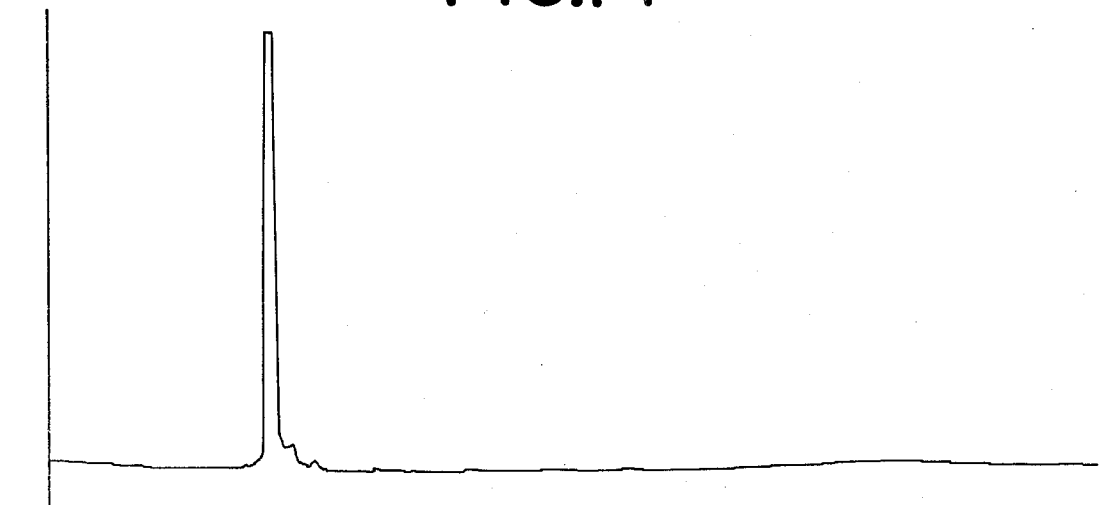
GLC PROFILE FOR BULKED FRACTIONS 3-6 OF EXAMPLE III.

NMR SPECTRUM FOR EXAMPLE III.

IR SPECTRUM FOR EXAMPLE III.

BRANCHED C₁₃-ALK-1-EN-5-ONES, USE THEREOF IN PERFUMERY, PROCESS FOR PREPARING SAME AND INTERMEDIATES USED IN SAID PROCESS

BACKGROUND OF THE INVENTION

Our invention relates to compounds defined according to the generic structure:

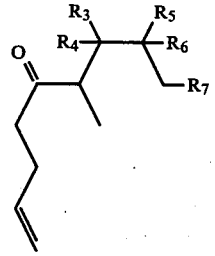

processes for producing same, intermediates useful in said processes and uses thereof in augmenting or enhancing the aroma of perfume compositions, perfumed articles and colognes (wherein $R_3$, $R_4$, $R_5$, $R_6$ and $R_7$ each represents the same or different methyl or hydrogen with the provisos that:

(i) the sum total of the carbon atoms of $R_3$, $R_4$, $R_5$, $R_6$ and $R_7$ is three;

(ii) when $R_7$ is methyl, then $R_5$ and $R_6$ are each methyl and (iii) when $R_7$ is hydrogen, then $R_3$ or $R_4$ is methyl.

Chemical compounds which can provide galbanum-like, fruity, pineapple-like, woody, ionone-like, bark-like, green, and oily-sweet aromas with floral undertones are highly desirable in the art of perfumery. Many of the natural materials which provide such fragrances and contribute such desired nuances to perfumery compositions and perfumed articles are high in cost, unobtainable at times, vary in quality from one batch to another and/or are generally subject to variations in natural products.

There is, accordingly, a continuing effort to find synthetic materials which will replace, enhance, or augment the fragrance notes provided by natural essential oils or compositions thereof. Unfortunately many of the synthetic materials which can provide such nuances either have the desired nuances only to a relatively small degree or they contribute undesirable or unwanted odor to the compositions.

U.S. Pat. No. 4,346,237 issued on Aug. 24, 1982 (incorporated by reference herein) discloses the production of unsaturated branched ketones according to the reaction:

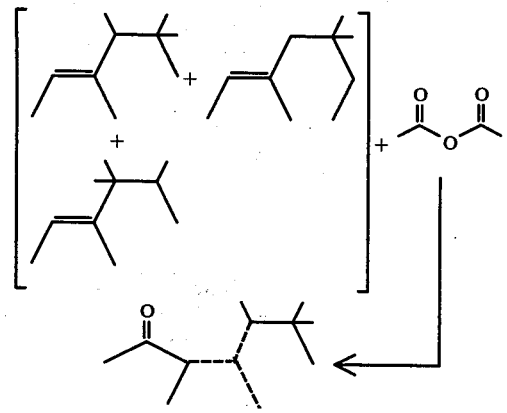

wherein in each of the structures containing dashed lines, the structures represent mixtures of molecules wherein in each of the molecules, one of the dashed lines represents a carbon-carbon double bond and each of the other of the dashed lines represents a carbon-carbon single bond. These compounds so produced are indicated to be useful for their organoleptic properties in augmenting or enhancing the aroma or taste of consumable materials including perfume compositions, colognes and perfumed articles. It is noteworthy that the compounds defined according to the structure:

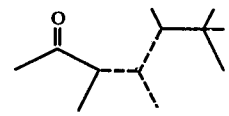

have unsaturation in the structure and, in addition, have unsaturation at the "3" or "4" position in the structure and have the location of the "keto" group at the "2" position; and, in addition, contain 12 carbon atoms.

Nothing in the prior art discloses the compounds defined according to the genus:

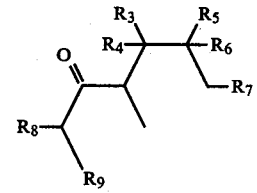

wherein $R_3$, $R_4$, $R_5$, $R_6$ and $R_7$ represent hydrogen or methyl with the provisos that:

(i) the sum total of carbon atoms in $R_3$, $R_4$, $R_5$, $R_6$ and $R_7$ is three;

(ii) when $R_7$ is methyl, then $R_5$ and $R_6$ are both methyl, and (iii) when either $R_3$ or $R_4$ is methyl, then $R_7$ is hydrogen and wherein $R_8$ represents hydrogen, acetyl, alkoxyacyl, hydroxyacyl, or alkali metal carboxylate; and $R_9$ is hydrogen or allyl with the additional proviso that $R_8$ and $R_9$ are not both hydrogen, or the subgenus having the structure:

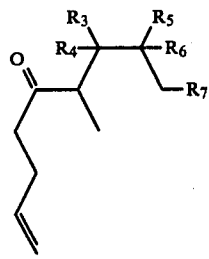

for use in augmenting or enhancing the aroma of perfume compositions, perfumed articles and colognes or the subgenera defined according to the structure:

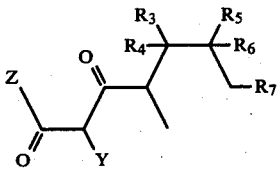

wherein Y is hydrogen or allyl and wherein Z represents methyl, alkoxy or alkali metal oxy or hydroxy useful as intermediates in preparing the compounds defined according to the structure:

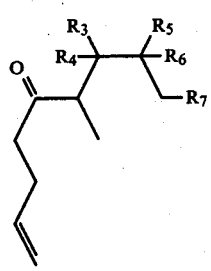

The compounds of our invention defined according to the structure:

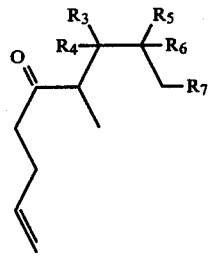

are prepared using as a precursor the compounds defined according to the generic structure:

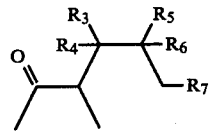

the preparation of which is disclosed in application for U.S. Pat. Ser. No. 345,665 filed on Feb. 4, 1982, the disclosure of which is incorporated by reference herein.

These compounds, in turn, are prepared using as an original precursor, "diisoamylene".

"Diisoamylene" is indicated to be synthesized in the following references:

(i)—Murphy & Lane, Ind. Eng. Chem., Prod. Res. Dev., Vol. 14, No. 3, 1975, p. 167 (Title: Oligomerization of 2-Methyl-2-Butene in Sulfuric Acid and Sulfuric-Phosphoric Acid Mixtures).

(ii)—Whitmore & Mosher, Vol. 68, J. Am. Chem. Soc., February, 1946, p. 281 (Title: The Depolymerization of 3,4,5,5-Tetramethyl-2-Hexene and 3,5,5-Trimethyl-2-Heptene in Relation to the Dimerization of Isoamylenes).

(iii)—Whitmore & Stahly, Vol. 67, J. Am. Chem. Soc., December, 1945, p. 2158 (Title: The Polymerization of Olefins. VIII The Depolymerization of Olefins in Relation to Intramolecular Rearrangements. II).

(iv)—U.S. Pat. No. 3,627,700, issued on Dec. 14, 1971, (Zuech).

(v)—U.S. Pat. No. 3,538,181, issued on Nov. 3, 1970, (Banks).

(vi)—U.S. Pat. No. 3,461,184 issued on Aug. 12, 1969 (Hay, et al).

(vii)—Gurwitsch, Chemische Berichte, 1912, Vol. 2, p. 796 (Production of Di-isoamylene From Isoamylene Using Mercury Acetate Catalyst).

United Kingdom Patent No. 796,130 published on June 4, 1958 discloses the synthesis of polyalkylindanes by means of, interalia, reacting alpha-methylstyrene with trimethylethene (2-methyl-butene-2) in the presence of an acid catalyst such as sulfuric acid or boron trifluoride methyletherate. It is further indicated that such compounds are useful intermediates in the production of perfumery compounds. Apparently, however, the more volatile diisoamylenes produced as side-products in the reaction of 2-methyl-butene-2 with alpha-methylstyrene are discarded.

The diisoamylene useful as a starting material in the instant case may be distilled from the reaction product (as see Example A infra) at a temperature in the range of 36°-40° C.; a liquid temperature in the range of 74°-94° C. and a pressure of 4-5 mm/Hg.

BRIEF DESCRIPTION OF THE DRAWINGS

FIG. 1D represents the GLC profile for the reaction product of Example A using a sulfuric acid catalyst and an alpha-methylstyrene diluent at 35° C. according to the conditions of United Kingdom Patent Specification No. 796,130 (crude reaction product) wherein isoamylene is dimerized to produce diisoamylene.

FIG. 1E represents the GLC profile for the reaction product of Example A using a sulfuric acid catalyst at 35° C. and an alpha-methylstyrene diluent according to the conditions of United Kingdom Patent Specification No. 796,130 (distilled reaction product) wherein isoamylene is dimerized to produce diisoamylene. The distillation range of the diisoamylene thus produced is as follows: vapor temperature 36°–40° C.; liquid temperature 74°–94° C.; and pressure 4–5 mm/Hg.

FIG. 4 represents the NMR spectrum for Peak 2 of the GLC profile of Peak 1B.

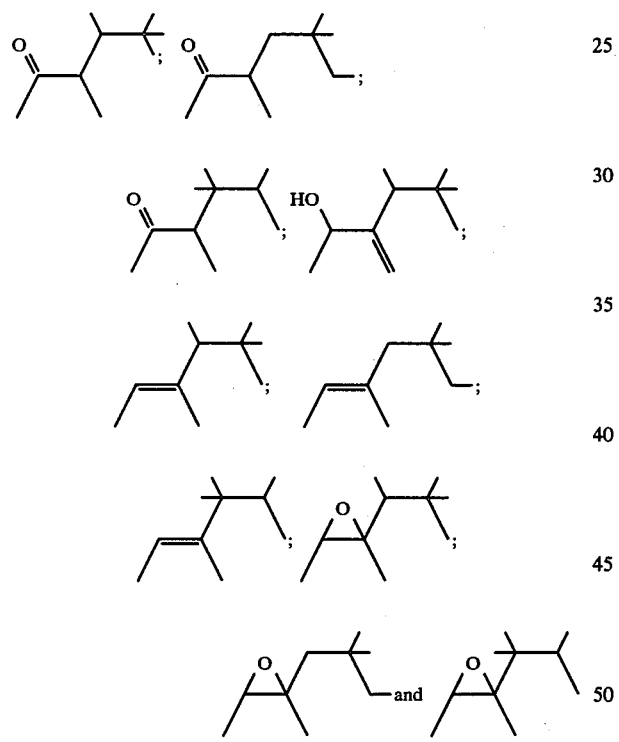

Figure 5:
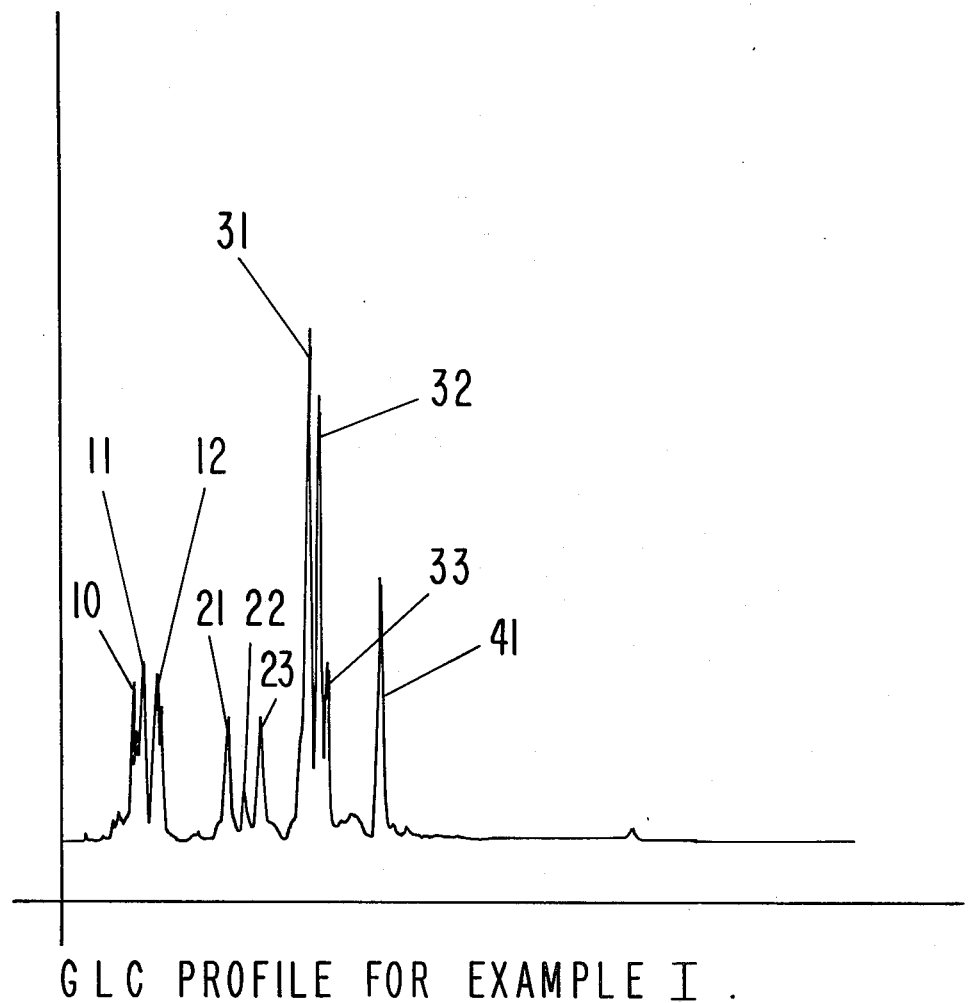
FIG. 5 is the GLC profile for the reaction product of Example I containing the compounds having the structures.
Figure 6:
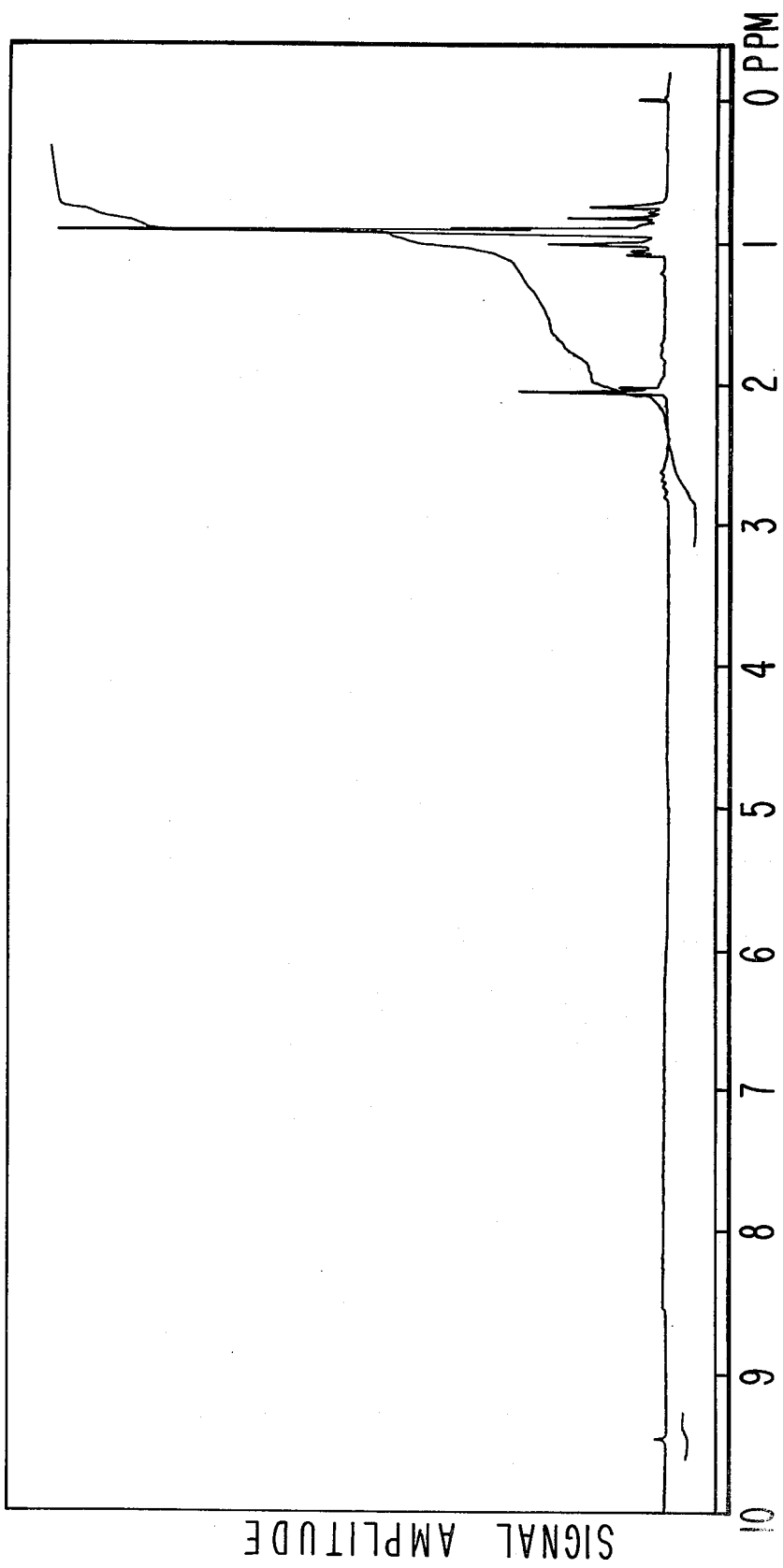

FIG. 6 is the NMR spectrum for Peaks 31, 32 and 33 of the GLC profile of FIG. 5 containing the compounds having the structures:

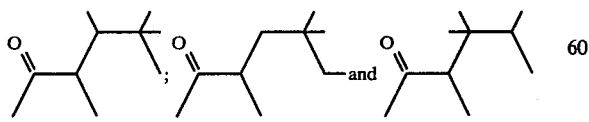

FIG. 7 is the infra-red spectrum for Peaks 31, 32 and 33 of FIG. 5, the GLC profile of the reaction product of Example I containing the compounds having the structures:

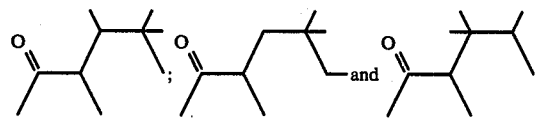

FIG. 8 is the NMR spectrum for Peaks 21, 22 and 23 of FIG. 5, the GLC profile of the reaction product of Example I containing the compounds having the structures:

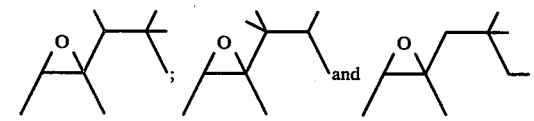

FIG. 9 is the infra-red spectrum for Peaks 21, 22 and 23 of the GLC profile of FIG. 5 which is the GLC profile of the reaction product of Example I containing the compounds having the structures:

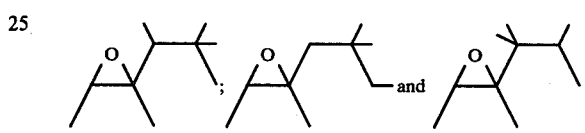

FIG. 10 is the GLC profile for fraction 5 of the distillation product of the reaction product of Example II containing the compounds defined according to the structures:

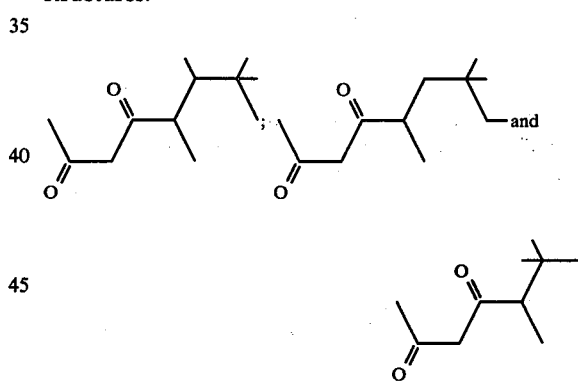

Figure 11:
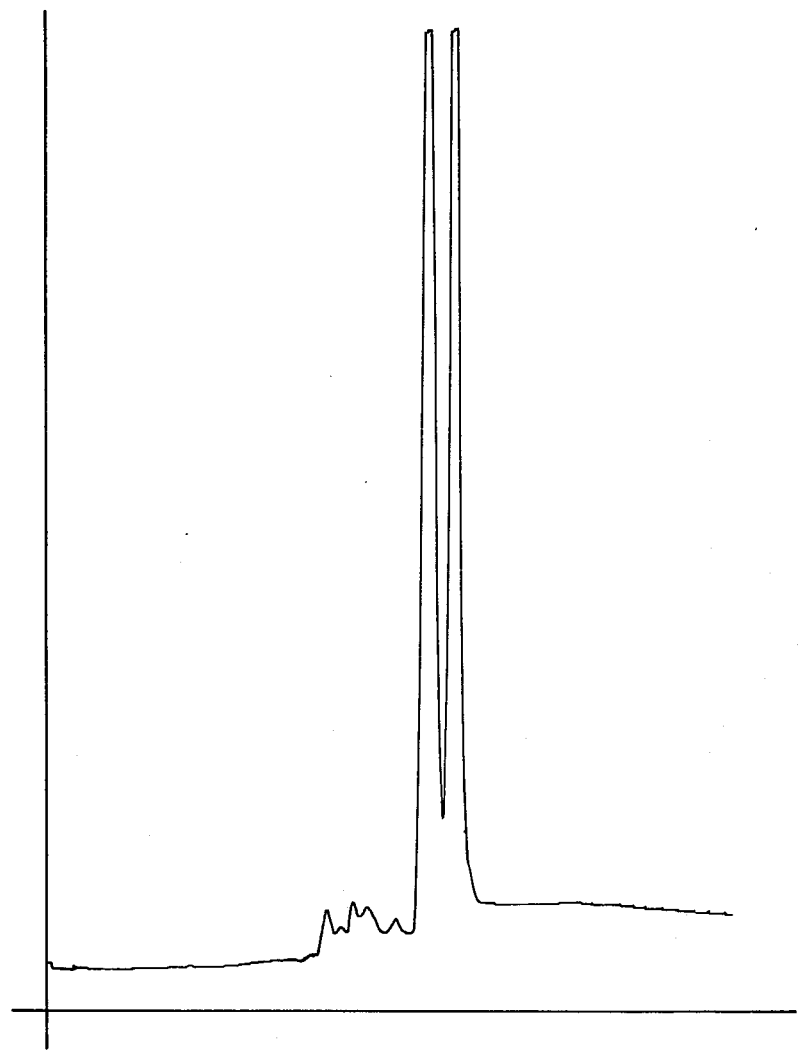

FIG. 11 is the GLC profile for fraction 6 of the distillation product of the reaction product of Example II containing the compounds having the structures:

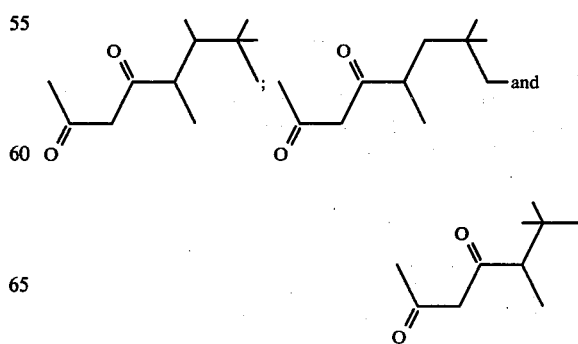

FIG. 12 is the GLC profile for fraction 7 of the distillation product of the reaction product of Example II containing the compounds having the structures:

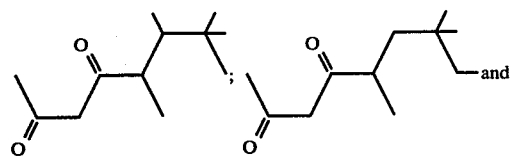

FIG. 13 is the GLC profile for the crude reaction product of Example III (conditions: 6′×0.25″ 12% SF-96 column programmed at 80°–220° C. at 16° C. per minute) containing the compounds having the structures:

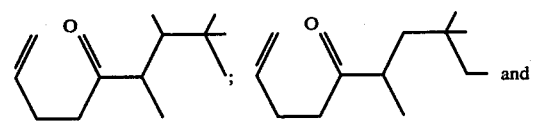

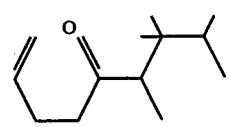

FIG. 14 is the GLC profile for bulked fractions 3–6 of the distillation product of the reaction product of Example III containing the compounds having the structures:

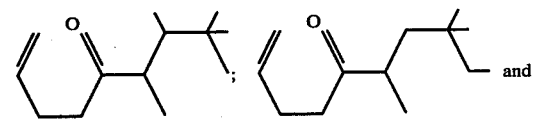

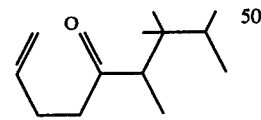

(conditions: 6′×0.25″ 12% SF-96 column programmed at 80°–220° C. at 16° C. per minute).

Figure 15:
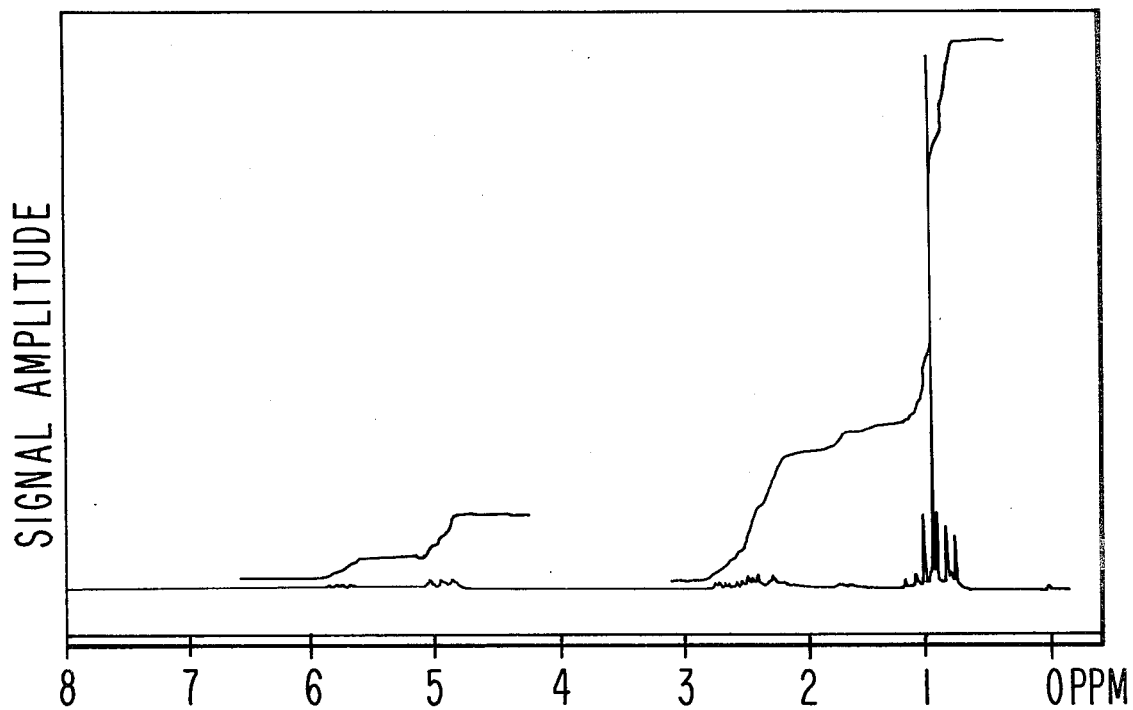

FIG. 15 is the NMR spectrum for bulked fractions 3–6 of the distillation product of the reaction product of Example III containing the compounds having the structures:

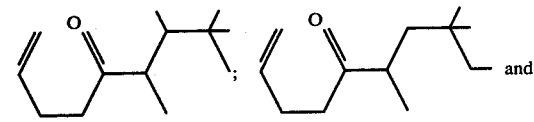

-continued

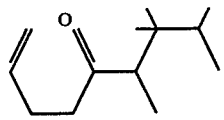

(conditions: Solvent: CFCl₃; Field Strength: 100 MHz).

Figure 16:
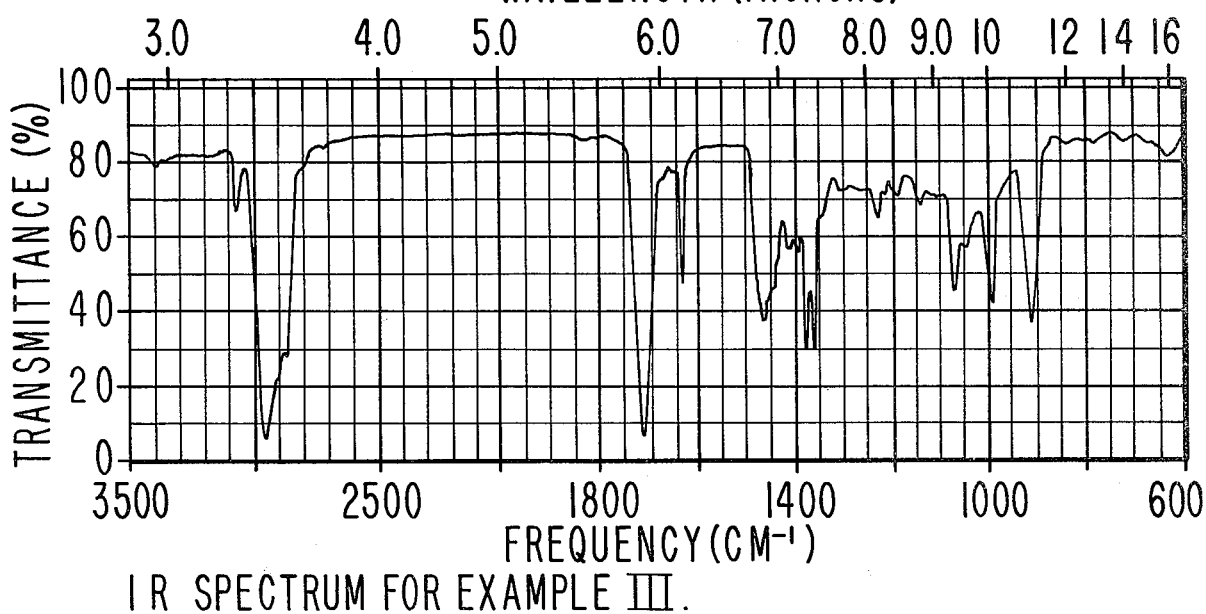

FIG. 16 is the infra-red spectrum for fraction 3 of the distillation product of the reaction product of Example III containing the compounds having the structures:

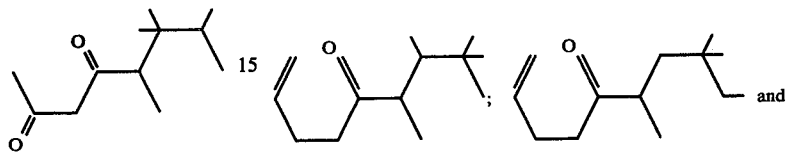

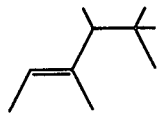

DETAILED DESCRIPTION OF THE DRAWINGS

FIG. 1E is the GLC profile for the reaction product of Example A-1 wherein in dimerizing isoamylene to form diisoamylene, sulfuric acid catalyst is used at a temperature of 35° C. and an alpha-methyl styrene diluent is used according to the conditions of United Kingdom Patent Specification No. 796,130. The distillation range for the diisoamylene is 36°–40° C. vapor temperature and 74°–94° C. liquid temperature and a pressure of 4–5 mm/Hg. The Peak indicated by reference numeral "1" and reference numeral "2" are peaks signifying one of the isomers:

with the isomer having the structure:

being the most prevalent of the three isomers having the structures:

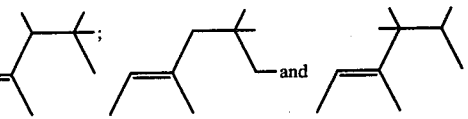

FIG. 5 is the GLC profile for the reaction product of Example I. In FIG. 5, the Peaks indicated by reference numerals "10", "11" and "12" are for the "starting material", the diisoamylene peaks having the structures:

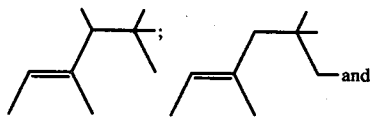

The Peaks indicated by reference numerals "21", "22" and "23" are those for the epoxy compounds created as a result of the oxidation having the structures:

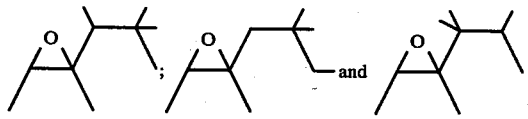

The Peaks in FIG. 5 indicated by reference numerals "31", "32" and "33" are those for the saturated branched ketones having the structures:

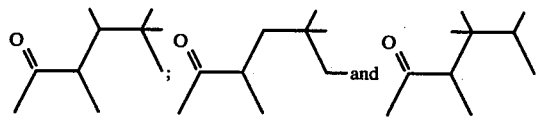

Peak 41 in FIG. 5 is the Peak which signifies the unsaturated alcohol defined according to the structure:

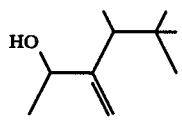

THE INVENTION

It has now been determined that certain branched $C_{13}$-alk-1-en-5-ones defined according to the generic structure:

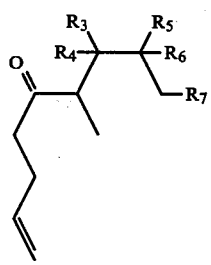

wherein $R_3$, $R_4$, $R_5$, $R_6$ and $R_7$ represent hydrogen or methyl with the provisos that:
(i) the sum total of carbon atoms in $R_3$, $R_4$, $R_5$, $R_6$ and $R_7$ is three;
(iii) when $R_7$ is methyl, then $R_5$ and $R_6$ are both methyl, and
(iii) when either $R_3$ or $R_4$ is methyl, then $R_7$ is hydrogen which include compounds defined according to the structures:

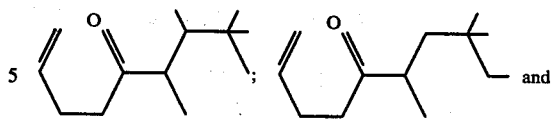

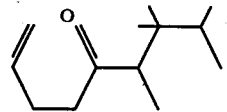

are capable of imparting or augmenting or enhancing a variety of fragrances in and to certain consumable materials including perfume compositions, perfumed articles and colognes.

Briefly, our invention contemplates augmenting or enhancing fragrances of such consumable materials as perfumes, perfumed articles (e.g. solid or liquid anionic, cationic, nonionic or zwitterionic detergents, cosmetic powders, fabric softener compositions, fabric softener articles, hair conditioners, perfumed plastics and floor waxes) and colognes by adding thereto a small but effective amount of at least one of the compounds defined according to the generic structure:

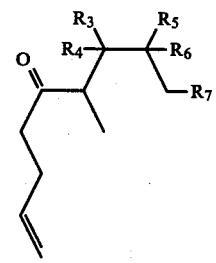

wherein $R_3$, $R_4$, $R_5$, $R_6$ and $R_7$ represent the same or different hydrogen or methyl with the provisos that:
(i) when $R_7$ is methyl, then $R_5$ and $R_6$ are each methyl;
(ii) with the sum total of the carbon atoms in $R_3$, $R_4$, $R_5$, $R_6$ and $R_7$ being three; and
(iii) when $R_7$ is hydrogen, then $R_3$ or $R_4$ is methyl or represented individually be the compounds:

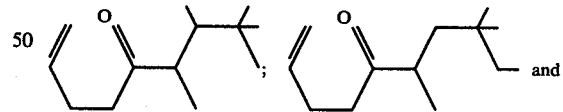

The foregoing compounds will hereinafter be indicated herein to be branched $C_{13}$-alk-1-en-5-ones.

The branched $C_{13}$-alk-1-en-5-ones of our invention augment or enhance galbanum-like, fruity, pineapple-like, woody, ionone-like, bark-like, green and oily, sweet aromas with floral undertones. The branched $C_{13}$-alk-1-en-5-ones of our invention are useful accordingly in "galbanum" type fragrances. Furthermore, the branched $C_{13}$-alk-1-en-5-ones of our invention have unexpected and unobvious stability particularly in the presence of strong oxidizing agents such as hypochlorite bleach solutions. Thus, the branched C$_{13}$-alk-1-en-5-ones of our invention can be used particularly to augment or enhance the aroma of perfumed bleach compositions particularly perfumed hypochlorite bleach compositions.

The branched C$_{13}$-alk-1-en-5-ones of our invention defined according to the structures:

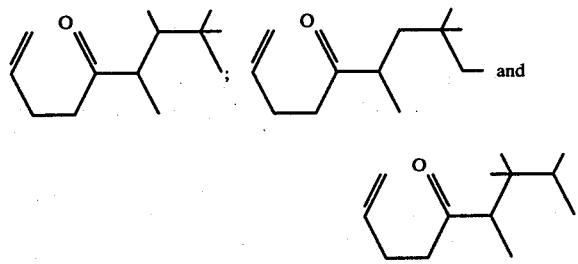

may be prepared using a novel process of our invention and certain intermediates produced during the process of our invention are novel compounds in and of themselves, e.g. intermediates defined according to the generic structure:

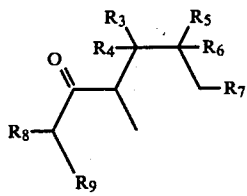

wherein Y is hydrogen or allyl and wherein Z represents methyl, C$_1$–C$_5$ alkoxy, hydroxy and alkali metaloxy such as sodiumoxy, potassiumoxi and lithiumoxi.

The branched C$_{13}$-alk-1-en-5-ones of our invention defined according to the structures:

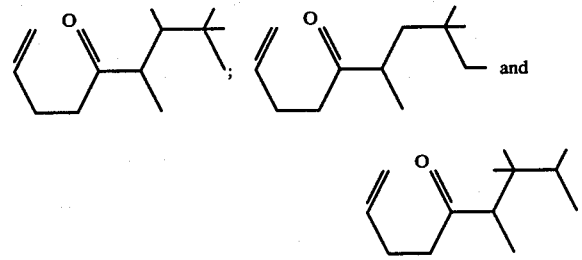

may be prepared by first reacting 2-methyl-2-butene in the presence of an acidic catalyst which may be a Lewis acid such as zinc chloride, aluminum chloride, aluminum bromide, diethyl aluminum chloride, diethyl aluminum bromide, ethyl dialuminum chloride and ethyl dialuminum bromide, boron trifluoride, boron trifluoride etherate or any other catalyst enumerated in the following references:

(i)—Murphy & Lane, Ind. Eng. Chem., Prod. Res. Dev., Vol. 14, No. 3, 1975, p. 167 (Title: Oligomerization of 2-Methyl-2-Butene in Sulfuric Acid and Sulfuric-Phosphoric Acid Mixtures).

(ii)—Whitmore & Mosher, Vol. 68, J. Am. Chem. Soc., February, 1946, p. 281 (Title: The Depolymerization of 3,4,5,5-Tetramethyl-2-Hexene and 3,5,5-Trimethyl-2-Heptene in Relation to the Dimerization of Isoamylenes).

(iii)—Whitmore & Stahly, Vol. 67, J. Am. Chem. Soc., December, 1945, p. 2158 (Title: The Polymerization of Olefins. VIII The Depolymerization of Olefins in Relation to Intramolecular Rearrangements. II).

(iv)—U.S. Pat. No. 3,627,700, issued on Dec. 14, 1971, (Zuech).

(v)—U.S. Pat. No. 3,538,181, issued on Nov. 3, 1970, (Banks).

(vi)—U.S. Pat. No. 3,461,184 issued on Aug. 12, 1969 (Hay, et al).

(vii)—Gurwitsch, Chemische Berichte, 1912, Vol. 2, p. 796 (Production of Di-isoamylene From Isoamylene Using Mercury Acetate Catalyst).

thereby forming the compounds having the structures:

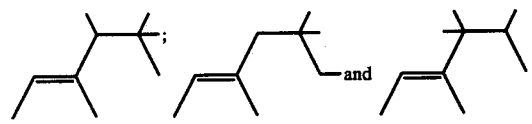

Then one or more of the compounds having the structures:

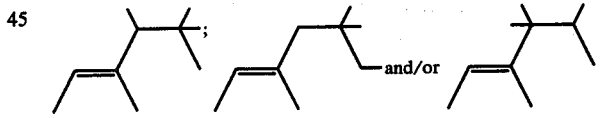

is then oxidized using a formic acid/concentrated hydrogen peroxide reagent according to the reaction:

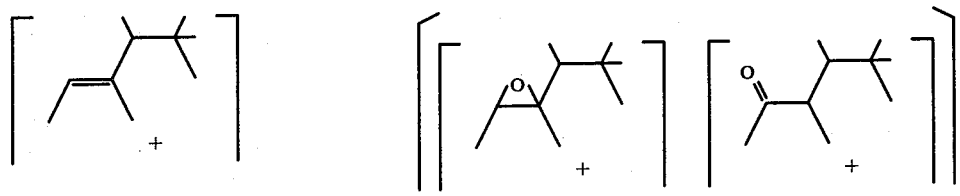

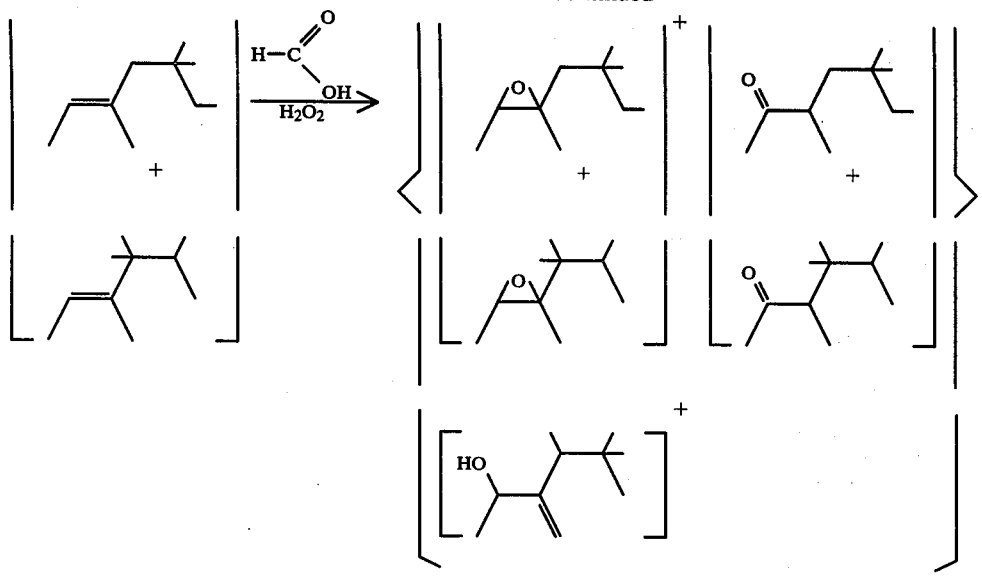

It is preferred that the concentration of diisoamylene:formic acid be between 1:1 and about 3:1 and the mole ratio of diisoamylene:hydrogen peroxide be between about 1:1 up to about 4:1 moles diisoamylene:-moles hydrogen peroxide.

It is preferred that the concentration of hydrogen peroxide be in the range of from about 30% up to about 55% with a preferred concentration (weight:weight in water) of hydrogen peroxide being about 50%. Too low a concentration of hydrogen peroxide will not cause the proper reaction to be effected and too high a concentration of hydrogen peroxide is dangerous to use.

It is preferred that the reaction temperature be in the range of from about 45° C. up to about 75° C. with the most preferred range being from 50° up to 70° C. Higher temperatures of reaction give rise to shorter periods of time but less controllable reactions. Thus, at 50° C. the reaction time using a 50% hydrogen peroxide solution is 4.5 hours.

At the end of the reaction, the reaction mass is neutralized whereby any excess hydrogen peroxide is removed from the reaction mass. The reaction mass is then neutralized, e.g. using saturated sodium chloride solution, and then distilled whereby the desired fractions containing the ketones having the structures:

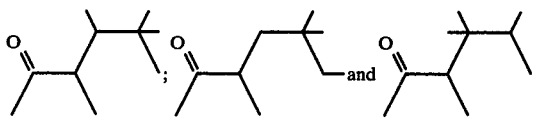

are removed at a vapor temperature of 95°-100° C.; a liquid temperature of 109°-120° C. and a pressure of 50 mm/Hg.

The foregoing process is specifically described in application for U.S. patent Ser. No. 345,665 filed on Feb. 4, 1982, the disclosure of which is incorporated by reference herein.

The resulting ketones defined according to the structures:

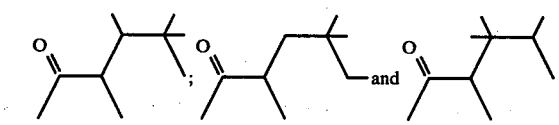

or defined according to the generic structure:

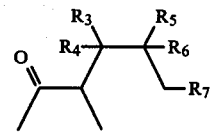

are then reacted either individually or in combination, according to the process of our invention with at least one compound defined according to the structure:

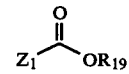

wherein $Z_1$ represents methyl or $-OR_{10}$ and wherein $R_{10}$ represents $C_1-C_5$ alkyl and wherein $R_{19}$ represents $C_1-C_5$ alkyl in order to form at least one compound defined according to the generic structure:

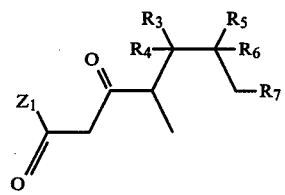

At least one of the compounds defined according to the generic structure:

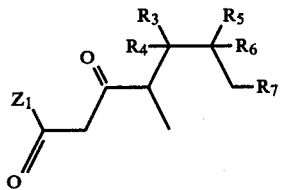

is then reacted with the allylic halide defined according to the structure:

(wherein X is chloro, bromo or iodo with the proviso that when $Z_1$ is methyl, when X represents bromo or iodo) in order to produce at least one compound defined according to the generic structure:

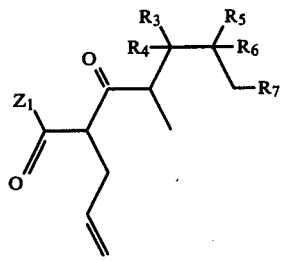

Depending on whether Z is $-OR_{10}$ or methyl, the next sequence of reactions is either a retro-Claisen reaction or a decarboxylation reaction.

Thus, according to one embodiment of the process of our invention, at least one compound having the structure:

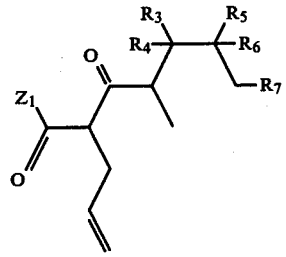

is reacted with an alkali metal alkoxide by means of a retro-Claisen reaction whereby at least one compound defined according to the structure:

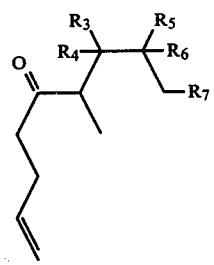

is formed directly.

In a second embodiment of our invention, the compound having the structure:

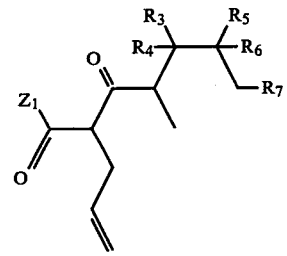

wherein Z is $-OR_{10}$ is hydrolyzed using base in order to form at least one of the compounds defined according to the structure:

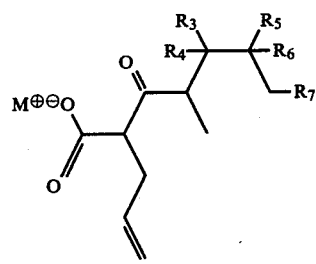

wherein M represents alkali metal such as sodium, potassium and lithium. The compound having the structure:

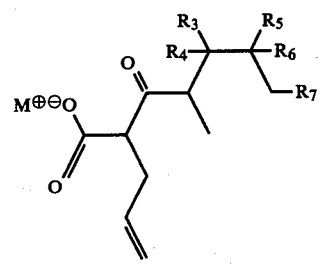

is then acidified to form at least one carboxylic acid having the structure:

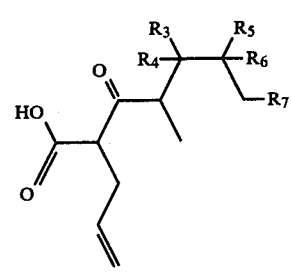

which, in turn, is then decarboxylated to form at least one of the compounds defined according to the structure:

17

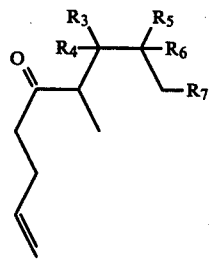

Thus, our process is embodied in the following generic reaction scheme:

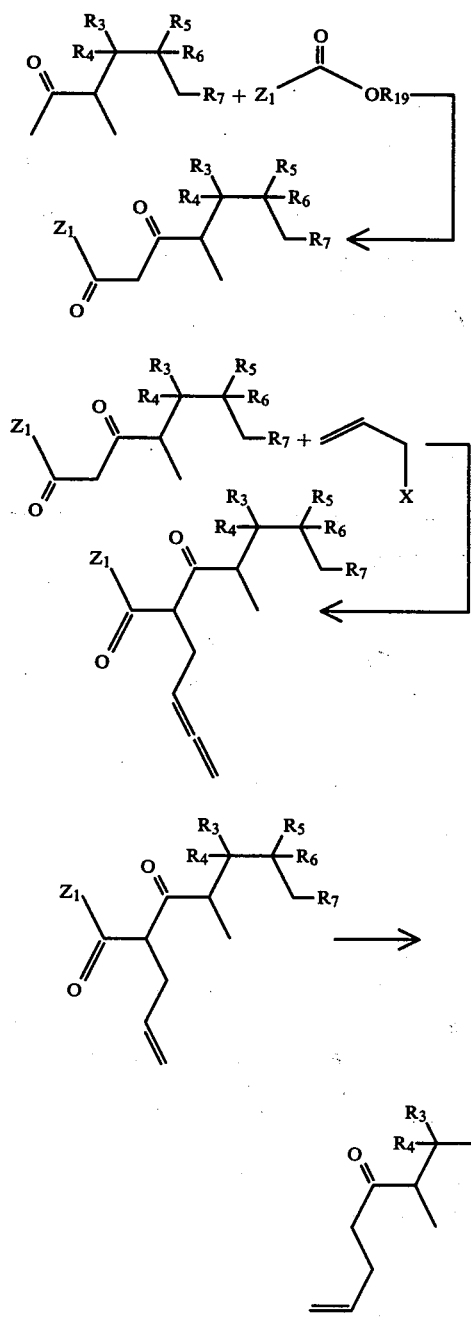

18

As stated supra, the last reaction (iii) may be a one-step retro-Claisen where $Z_1$ is methyl or it may be carried out in several steps if $Z_1$ is —$OR_{10}$.

Accordingly, our process may be specifically shown using two alternative reaction sequences.

Reaction Sequence I:

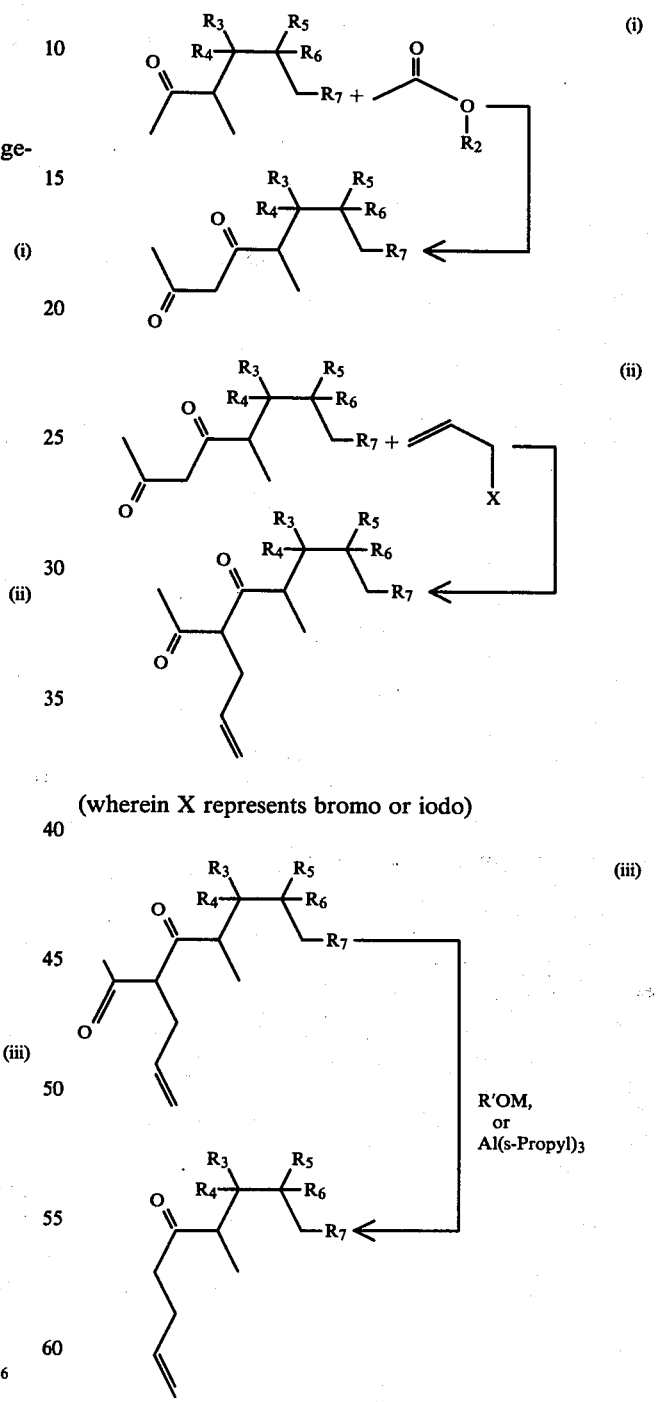

(wherein X represents bromo or iodo)

(wherein $M_1$ is sodium, potassium or lithium and R′ is lower alkyl including methyl, ethyl, n-propyl, i-propyl, n-butyl, i-butyl and t-butyl or R′$OM_1$ can be replaced by aluminum triisopropylate).

Reaction Sequence II

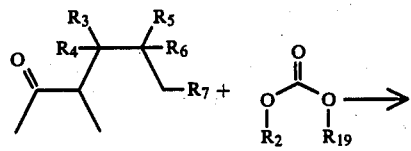
(i)

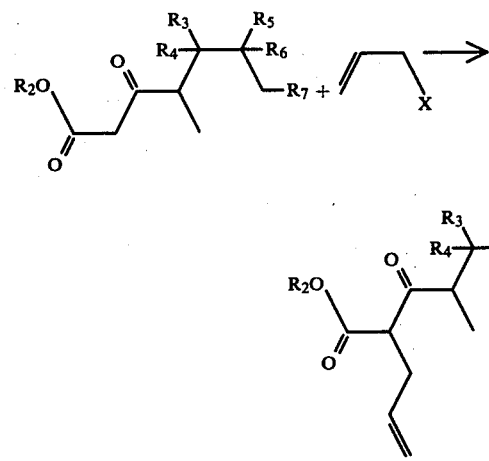
(ii)

(wherein $R_2$ and $R_{19}$ are the same or different and each represents $C_1$–$C_5$ alkyl)

(wherein X is chloro, bromo or iodo)

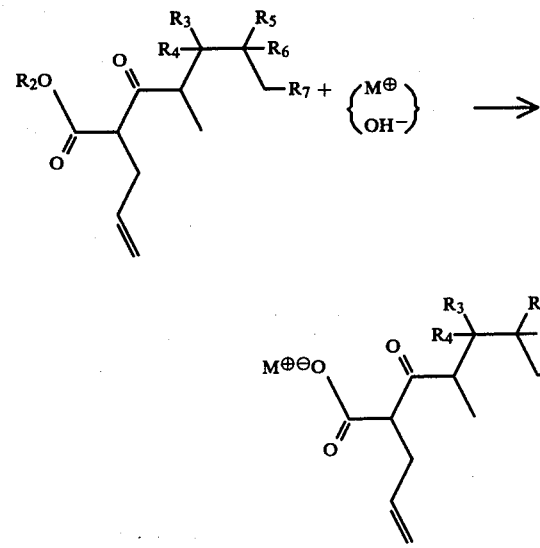
(iii)

(wherein M represents alkali metal such as sodium, potassium or lithium)

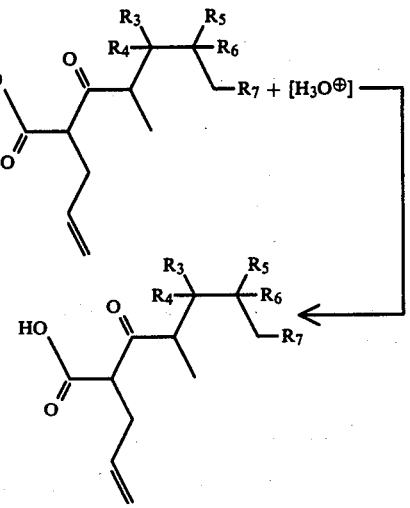
(iv)

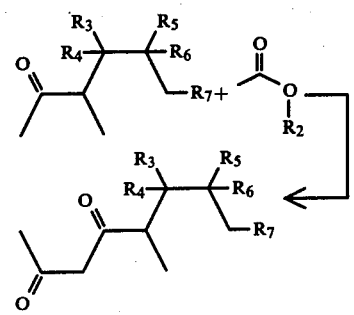
(v)

Referring to reaction sequence I and referring to the first reaction therein, to wit:

$R_2$ may be $C_1$–$C_5$ lower alkyl including methyl, ethyl, 1-propyl, 2-propyl, 1-butyl, 2-butyl, 1-methyl-2 propyl and 2-methyl-2-propyl. The reaction takes place at a temperature in the range of from about 20° C. up to about 50° C. and a pressure in the range of from about 0.7 atmospheres up to about 5 atmospheres, preferably at a temperature of from about 30° up to about 40° C. and at 1 atmosphere pressure. The reaction takes place using an alkali metal alkoxide catalyst such as sodium methoxide, sodium isopropoxide, potassium methoxide, potassium isopropoxide and aluminum triisopropylate.

The mole ratio of ketone having the structure:

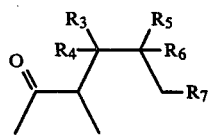

to alkyl acetate is between 1:1 and 1:2 with a preferred mole ratio of ketone compound:alkyl acetate of about 1:1.5. The mole ratio of alkali metal alkoxide:ketone compound is between 0.5:1 and 1:0.5 with a preferred mole ratio of alkali metal alkoxide:ketone compound being about 1:1.

In carrying out the reaction (ii) of this sequence I, to wit:

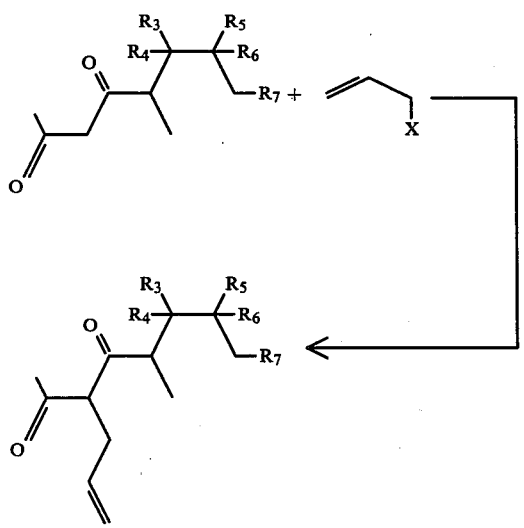

the ratio of diketone having the structure:

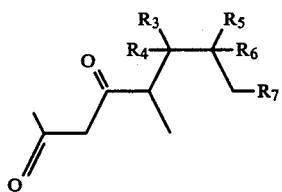

to the allyl halide having the structure:

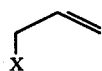

is between 1:1 and 1:2 with a preferred ratio of about 1:1. In this reaction, the allyl halide is one wherein X is bromo or iodo. Actually, allyl chloride can be used as a reactant but the allyl iodide or allyl bromide must be produced in situ. Accordingly, conveniently, allyl chloride may be used along with such a material as sodium iodide or sodium bromide whereby the allyl iodide or allyl bromide is produced in situ.

This reaction takes place at reflux conditions, preferably at a temperature in the range of from about 60° up to about 80° C., most conveniently at atmospheric pressure. However, pressures greater than or less than atmospheric pressure may be used. Accordingly, the pressure of reaction may vary from about 0.7 atmospheres up to about 10 atmospheres at reflux conditions. Higher temperatures of reaction give rise to shorter time periods of reaction. For example, when carrying out the reaction at 60°-70° C., the time of reaction is about 8 hours.

At the end of this reaction, the reaction mass is purified by means of solvent stripping. The reaction product is then further reacted by means of reaction (iii) to wit:

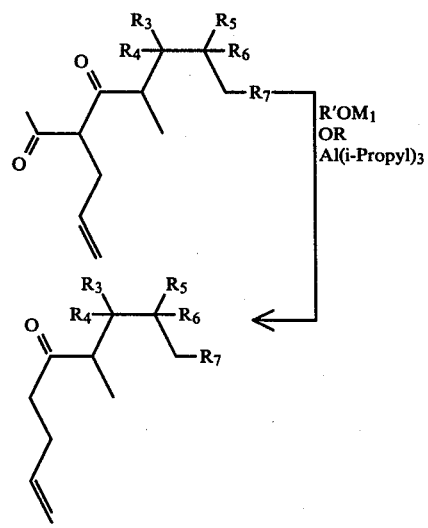

wherein $M_1$ is alkali metal such as sodium, potassium and lithium and $R'$ is lower alkyl such as methyl, ethyl, i-propyl, n-propyl, n-butyl, i-butyl and t-butyl or $R'OM_1$ can be replaced by aluminum triisopropylate. The reaction preferably takes place in aqueous solution. In place of the alkali metal alkoxide used, an aqueous alcoholic alkali metal hydroxide solution can be used. Thus, for example, one liter of 50% aqueous sodium hydroxide may be admixed with 500 ml water and 500 ml methyl alcohol and the resulting mixture is then admixed with the compound having the structure:

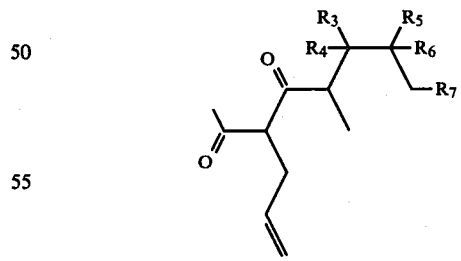

This reaction is carried out at a temperature of between 35° and 50° C.

The resulting product is then distilled from the reaction mass by means of fractional distillation at a vapor temperature of 108°-128° C. and a pressure of 3.0 mm/Hg.

Referring now to reaction sequence II, in carrying out the reaction (i), to wit:

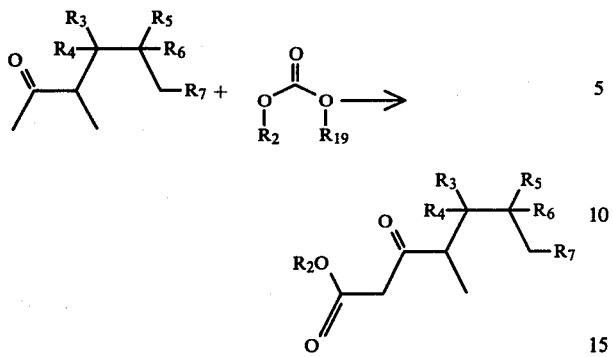

the dialkyl carbonate defined according to the structure:

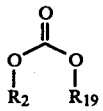

can be used as the solvent so that excess dialkyl carbonate is preferably used. The reaction is carried out using as an additional reagent, an alkali metal hydride such as sodium hydride, potassium hydride or an alkaline earth metal hydride catalyst such as calcium hydride or magnesium hydride. The reaction temperature may vary from 25° C. up to 100° C. but the reaction is preferably carried out at reflux conditions. The mole ratio of ketone derivative having the structure:

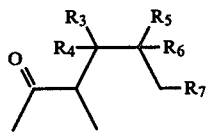

to alkali metal hydride or alkaline earth metal hydride: dialkyl carbonate may vary from about 1:2:1 up to about 1:2:2.

In carrying out the reaction of the thus-formed diketo ester defined according to the structure:

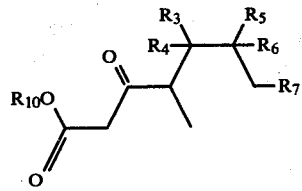

with the allyl halide having the structure:

wherein X is chloro, bromo or iodo, this reaction is carried out in the presence of an alkali metal alkoxide such as sodium ethoxide, sodium methoxide, potassium methoxide, potassium ethoxide or potassium t-butoxide or an alkali metal hydride such as sodium hydride, potassium hydride or lithium hydride or an alkaline earth metal hydride such as calcium hydride or magnesium hydride in order to form the substituted ketoester defined according to the structure:

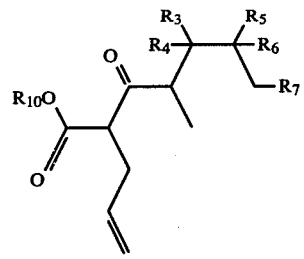

(wherein $R_{10}$ is $C_1$–$C_5$ alkyl).

The mole ratio of ketoester having the structure:

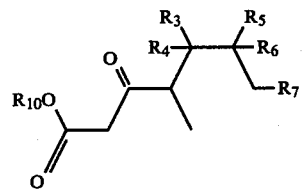

to allyl halide:alkali metal alkoxide or alkali metal hydride or alkaline earth metal hydride is preferably 1:1:1. This particular reaction preferably takes place in the presence of an inert solvent which will not react with the other reactant such as toluene, benzene or xylene.

The saponification of the substituted ketoester to form the substituted ketocarboxylic acid alkali metal salt defined according to the structure:

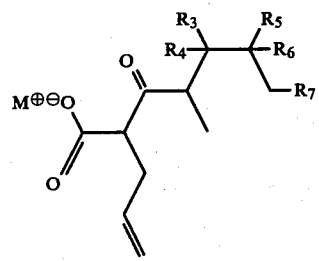

wherein M is alkali metal such as lithium, sodium or potassium, is carried out in the presence of a base such as sodium hydroxide, potassium hydroxide or lithium hydroxide in aqueous media according to standard saponification conditions. The resulting saponified material is then hydrolyzed in the presence of acid under standard hydrolysis conditions known in the art using such mineral acids as sulfuric acid or hydrochloric acid in order to form the substituted carboxylic acid defined according to the structure:

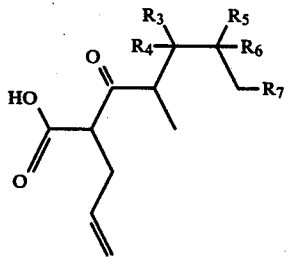

This material is then decarboxylated according to standard decarboxylation conditions in order to form at least one of the compounds defined according to the structure:

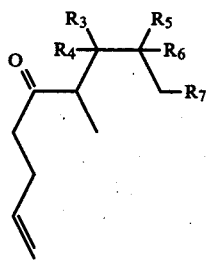

or individually, one of the compounds defined according to the structures:

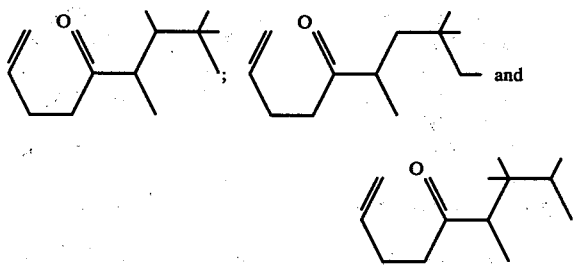

As olfactory agents, one or more of the branched $C_{13}$-alk-1-en-5-ones of our invention taken alone or in admixture can be formulated into or used as components of a "perfume composition" or can be used as components of a "perfumed article" or the perfume composition may be added to perfumed articles.

The term "perfume composition" is used herein to mean a mixture of organic compounds including, for example, alcohols, aldehydes, ketones (other than the ketones of our invention), nitriles, ethers, lactones, epoxides, natural essential oils, synthetic essential oils and hydrocarbons which are admixed so that the combined odors of the individual components produce a pleasant or desired fragrance. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation, and substances which retard evaporation and (d) topnotes which are usually low-boiling, fresh-smelling materials.

In perfume compositions, the individual component will contribute its particular olfactory characteristics, but the overall effect of the perfume composition will be the sum of the effects of each of the ingredients and, in certain instances, a synergistic effect as a result of the addition of certain ingredients. Thus, the individual compounds of this invention, or mixtures thereof, can be used to alter the aroma characteristics of a perfume composition, for example, by highlighting or moderating the olfactory reaction contributed by another ingredient in the composition.

The amount of one or more of the branched $C_{13}$-alk-1-en-5-ones of this invention which will be effective in perfume compositions depends on many factors including the other ingredients, their amounts and the effects which are desired. It has been found that perfume compositions containing as little as 0.05% of one or more of the branched $C_{13}$-alk-1-en-5-ones of this invention, or even less, can be used to impart interesting galbanum-like, fruity, pineapple-like, woody, ionone-like, bark-like, green, oily, sweet aromas with floral undertones to soaps, liquid or solid anionic, cationic drier-added fabric softener articles, (e.g. BOUNCE ®, a registered trademark of the Procter & Gamble Company of Cincinnati, Ohio), optical brightener compositions, hypochlorite bleach compositions, fragranced polymers, hair conditioners and other products. The amount employed can range up to 70% or even higher and will depend on considerations of cost, nature of the end product and the effect desired on the finished product and particular fragrance sought. Thus, for example, when fragrancing liquid bleach compositions containing alkali metal hypochlorite such as, for example, sodium hypochlorite or lithium hypochlorite, for example CLOROX ® (registered trademark of Clorox, Inc.), the amount employed can range as high as 100% of the fragrance involved in the liquid bleach. Indeed, a distinctive aspect of our invention is the use of one or more of the branched $C_{13}$-alk-1-en-5-ones of our invention in a stable liquid bleach composition.

One or more of the branched $C_{13}$-alk-1-en-5-ones of this invention taken alone or in admixture can be used alone or in a perfume composition as an olfactory component in detergents, soaps, space odorants and deodorants; perfumes; colognes, toilet waters; bath salts; hair preparations such as lacquers, brilliantines, pomades and shampoos; cosmetic preparations such as creams, deodorants, hand lotions, sun screens; powders such as talcs, dusting powders, face powders and the like; liquid bleaches such as sodium hypochlorite-containing bleaches; floor waxes, automobile aromas and automobile polish compositions. When used as an olfactory component of a perfumed article, as little as 0.01% of one or more of the branched $C_{13}$-alk-1-en-5-ones will suffice to impart an interesting galbanum-like, fruity, pineapple-like, woody, ionone-like, bark-like, green and oily sweet aroma with floral undertones. Generally no more than 1.5% based on the perfumed article is required to impart such aromas. However, in view of the rather low cost of the branched $C_{13}$-alk-1-en-5-ones of our invention, up to 100% of the perfume composition can be one or more of the branched $C_{13}$-alk-1-en-5-ones.

In summary, the range of the branched $C_{13}$-alk-1-en-5-ones of our invention in the perfumed article can be from 0.01% up to 1.5% or even higher.

In addition, the perfume composition can contain a vehicle or carrier for the branched $C_{13}$-alk-1-en-5-ones alone or with other ingredients. The vehicle can be a liquid such as a non-toxic alcohol such as ethanol, a glycol such as propylene glycol or the like. The carrier can be an absorbent solid such as a gum or components for encapsulating the composition such as gelatin which can be used to form a capsule wall surrounding the perfume oil as by means of coacervation with gelation or by means of formation of a polymer around the perfume oil as by polymerizing a urea formaldehyde polymer.

It will thus be apparent that the branched $C_{13}$-alk-1-en-5-ones of our invention can be used to alter, modify, augment or enhance sensory properties particularly organoleptic properties such as fragrances of a wide variety of consumable materials.

The following Examples A and I serve to illustrate processes for producing ketones useful in the process of making the branched $C_{13}$-alk-1-en-5-ones of our invention which precursor ketones are defined according to the generic structure:

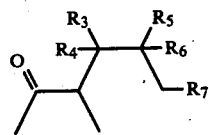

The following Examples II and III serve to illustrate processes for producing the branched $C_{13}$-alk-1-en-5-ones of our invention defined according to the structure:

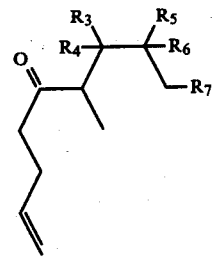

as well as intermediates therefor.

The examples commencing with Example III et seq. serve to illustrate the organoleptic uses of the branched $C_{13}$-alk-1-en-5-ones of our invention.

This invention is to be considered restricted to the examples only as indicated in the appended claims.

All parts and percentages given herein are by weight unless otherwise specified.

EXAMPLE A

Preparation of Diisoamylene Derivatives

Reaction:

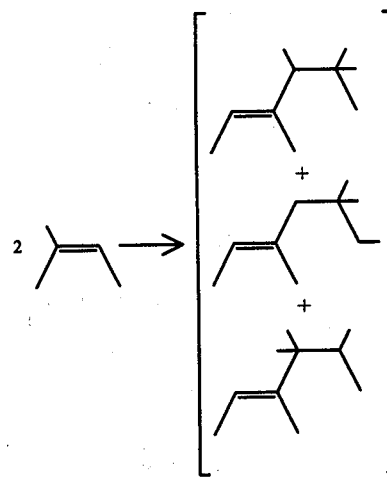

Diisoamylene is prepared according to one of the procedures set forth in the following references:

(i)—Murphy & Lane, Ind. Eng. Chem., Prod. Res. Dev., Vol. 14, No. 3, 1975, p. 167 (Title: Oligomerization of 2-Methyl-2-Butene in Sulfuric Acid and Sulfuric-Phosphoric Acid Mixtures).

(ii)—Whitmore & Mosher, Vol. 68, J. Am. Chem. Soc., February, 1946, p. 281 (Title: The Depolymerization of 3,4,5,5-Tetramethyl-2-Hexene and 3,5,5-Trimethyl-2-Heptene in Relation to the Dimerization of Isoamylenes).

(iii)—Whitmore & Stahly, Vol. 67, J. Am. Chem. Soc., December, 1945, p. 2158 (Title: The Polymerization of Olefins. VIII The Depolymerization of Olefins in Relation to Intramolecular Rearrangements. II).

(iv)—U.S. Pat. No. 3,627,700, issued on Dec. 14, 1971, (Zuech).

(v)—U.S. Pat. No. 3,538,181, issued on Nov. 3, 1970, (Banks).

(vi)—U.S. Pat. No. 3,461,184 issued on Aug. 12, 1969 (Hay, et al).

(vii)—Gurwitsch, Chemische Berichte, 1912, Vol. 2, p. 796 (Production of Di-isoamylene From Isoamylene Using Mercury Acetate Catalyst).

As an illustration and not by way of limitation, the following example sets forth the preparation of diisoamylenes useful in producing the methyl substituted oxohexane derivatives of our invention which are useful in producing the fragrances of our invention.

EXAMPLE A-I

Over a period of 10 hours, 2-methyl-2-butene is pumped through a $5' \times \frac{5}{8}''$ (0.625 inch) tube packed with 15.0 grams of polystyrene sulfonic acid catalyst at a temperature of 100° C. and a pressure of 400 psig.

The resulting material was distilled in a fractionation column in order to separate the diisoamylene from the higher molecular weight polymers which are formed during the reaction as by-products. This material distills at 36°–40° C. vapor temperature; 74°–94° C. liquid temperature and 4–5 mm/Hg pressure. This material will be used in the syntheses in the following Example II.

Figure 1A:
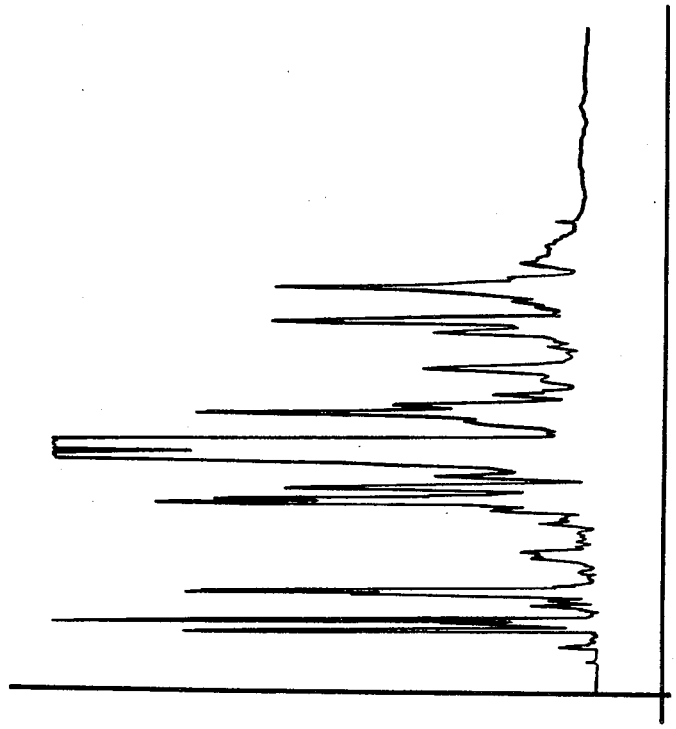
FIG. 1A represents the GLC profile for the reaction product of Example A using a 70% sulfuric acid catalyst at 35° C., wherein diisoamylene is produced by dimerizing isoamylene.

FIG. 1A represents the GLC profile for the reaction product of Example A using a 70% sulfuric acid catalyst at 35° C.

Figure 1B:
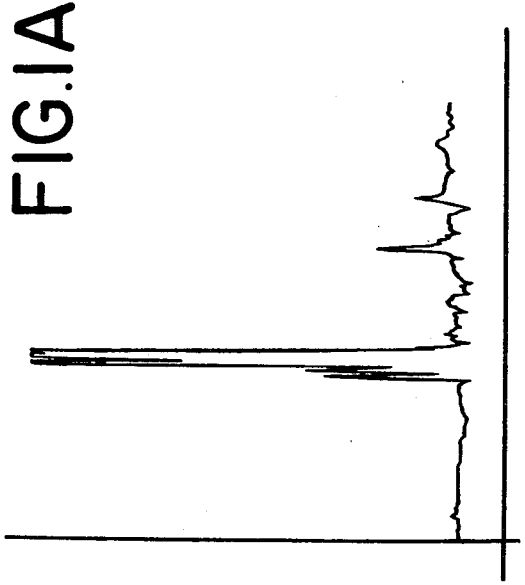
FIG. 1B represents the GLC profile for the reaction product of Example A using the Amberlyst ®15 acidic ion exchange resin catalyst at a temperature of 150° C. wherein isoamylene is dimerized to produce diisoamylene.

FIG. 1B represents the GLC profile for the reaction product of Example A using an Amberlyst ®15 acidic ion exchange catalyst at a temperature of 150° C.

Figure 1C:
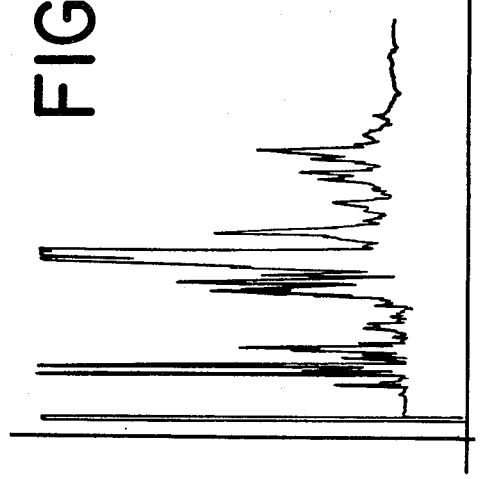
FIG. 1C represents the GLC profile for the reaction product of Example A using an Amberlyst ®15 catalyst at 100° C. wherein isoamylene is dimerized to produce diisoamylene.

FIG. 1C represents the GLC profile for the reaction product of Example A using an Amberlyst ®15 catalyst at 100° C.

FIG. 1D represents the GLC profile for the reaction product of Example A using a sulfuric acid catalyst and an alpha-methylstyrene diluent at 35° C. according to the conditions of United Kingdom Patent Specification No. 796,130 (crude reaction product).

FIG. 1E represents the GLC profile for the reaction product of Example A using a sulfuric acid catalyst at 35° C. and an alpha-methylstyrene diluent according to the conditions of United Kingdom Patent Specification No. 796,130 (distilled reaction product). Distillation range: 36°–40° C. vapor temperature for the diisoamylene; 74°–94° C. liquid temperature for the diisoamylene; and 4–5 mm/Hg pressure.

Figure 2A:
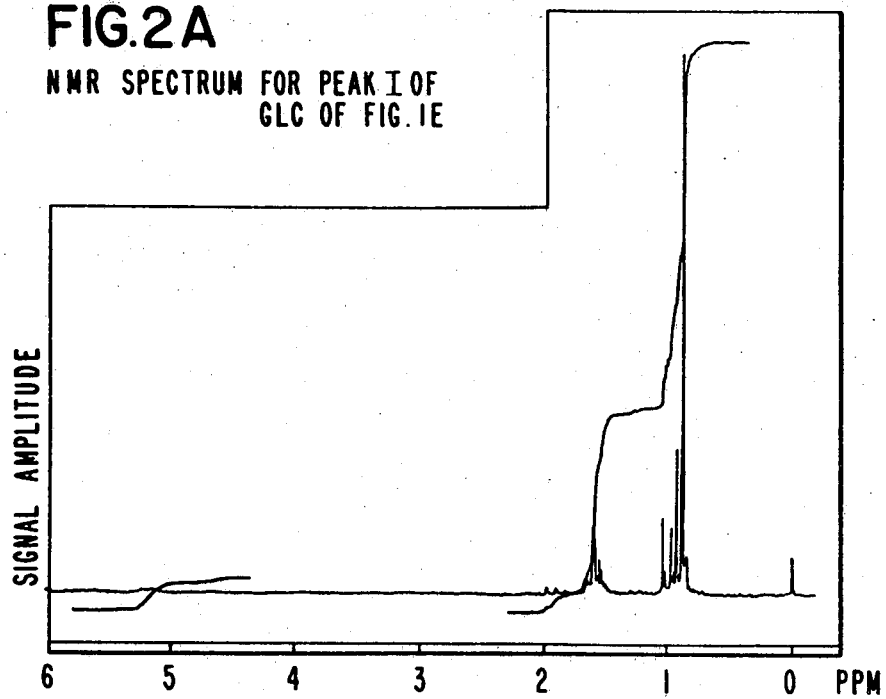
FIG. 2A represents the NMR spectrum for Peak 1 of the GLC profile of FIG. 1E.

FIG. 2A represents the NMR spectrum for Peak 1 for the GLC profile of FIG. 1E.

Figure 2B:
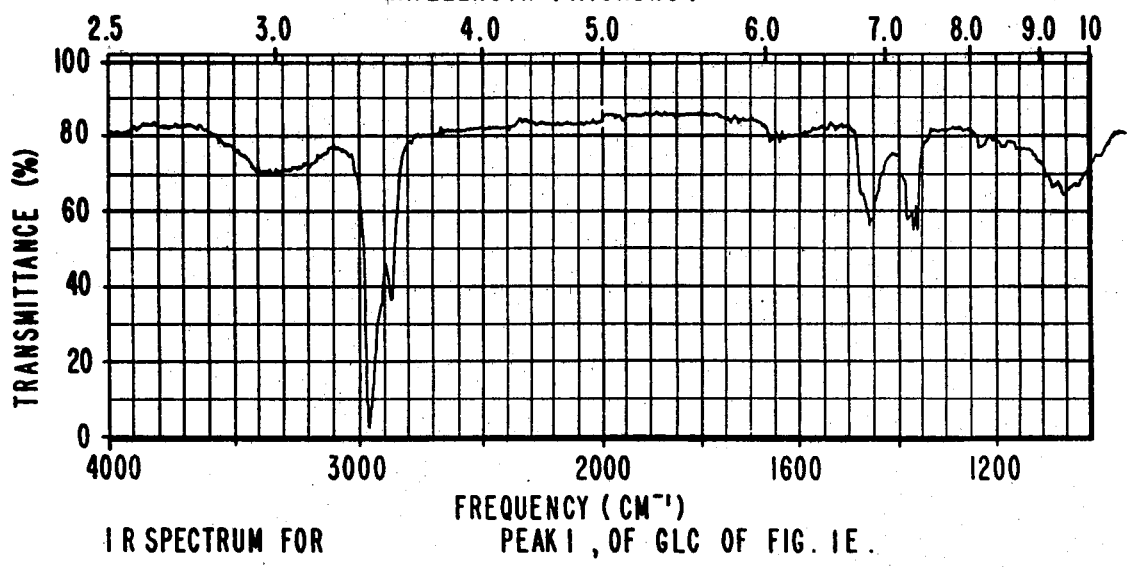
FIG. 2B represents the infra-red spectrum for Peak 1 of the GLC profile of FIG. 1E.

FIG. 2B represents the infra-red spectrum for Peak 1 of the GLC profile of FIG. 1E.

Figure 3A:
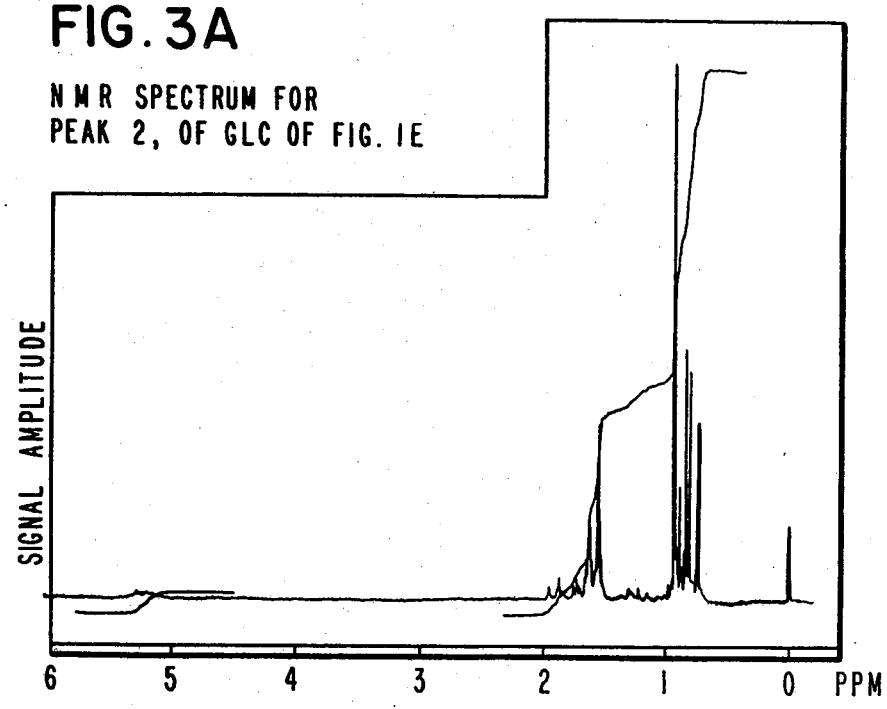
FIG. 3A represents the NMR spectrum for Peak 2 of the GLC profile of FIG. 1E.

FIG. 3A represents the NMR spectrum for Peak 2 of the GLC profile of FIG. 1E.

Figure 3B:
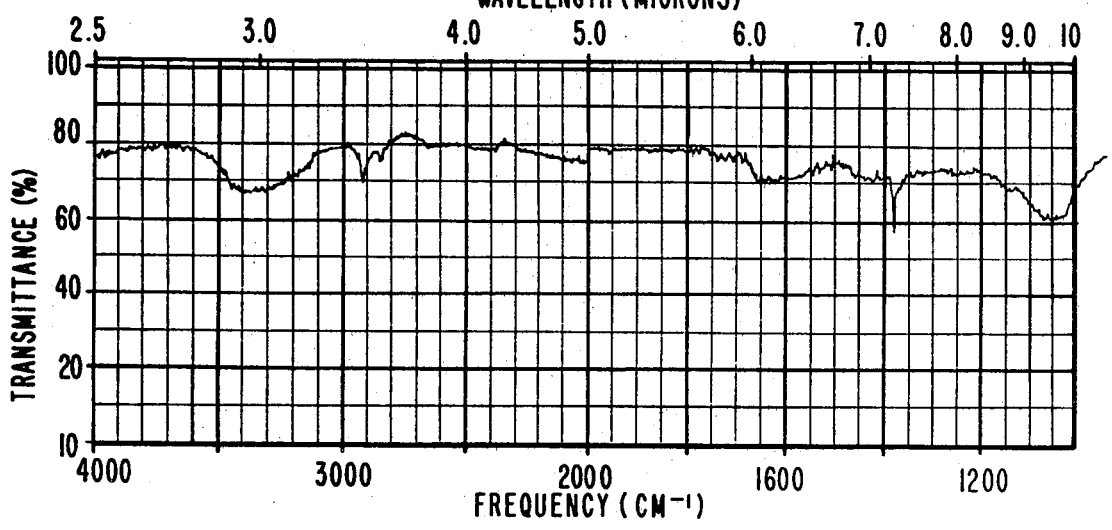
FIG. 3B represents the infra-red spectrum for Peak 2 of the GLC profile of FIG. 1E.

FIG. 3B represents the infra-red spectrum for Peak 2 of the GLC profile of FIG. 1E.

FIG. 4 represents the NMR spectrum for Peak 2 of the GLC profile of FIG. 1B.

EXAMPLE I

Preparation of Methyl Substituted Oxohexane Derivatives

Reaction:

Into a 3 liter reaction flask equipped with stirrer, thermometer, reflux condenser, dropping funnel, heating mantle and cooling bath is placed 1,000 grams of diisoamylene prepared according to Example A-I (distillation temperature: 36°–40° C. vapor temperature; 74°–94° C. liquid temperature at 4–5 mm/Hg pressure) and 375 grams of 90% formic acid. The resulting mixture is heated to 50° C. and then over a period of 1.25 hours 485 grams of 50% hydrogen peroxide is slowly added to the reaction mass while maintaining the reaction mass at a temperature in the range of 42°–69° C. After the addition of the hydrogen peroxide, the reaction mass is then heated at 50° C. for a period of 3.5 hours. At the end of the 3.5 hour period, the reaction mass is cooled to room temperature and 1 liter of a 25% aqueous sodium hydroxide solution is added to the reaction mass. The reaction mass is then again washed with 1 liter of 25% sodium hydroxide followed by 2 volumes of 500 ml saturated sodium chloride. The organic phase is then distilled on a 2′×1″ Goodloe column yielding the following fractions:

| Fraction Number | Vapor Temp. (°C.) | Liquid Temp. (°C.) | Pressure mm/Hg. | Reflux Ratio | Weight of Fraction (grams) |
|---|---|---|---|---|---|
| 1 | 54/60 | 93/105 | 25/35 | 9:1/9:1 | 25.8 |
| 2 | 64 | 105 | 35 | 9:1 | 30.9 |
| 3 | 68 | 105 | 45 | 9:1 | 36.4 |
| 4 | 80 | 107 | 50 | 9:1 | 32.2 |
| 5 | 88 | 107 | 50 | 9:1 | 36.2 |
| 6 | 93 | 109 | 50 | 9:1 | 36.3 |
| 7 | 95 | 109 | 50 | 9:1 | 39.0 |
| 8 | 96 | 110 | 50 | 9:1 | 34.9 |
| 9 | 96 | 111 | 50 | 9:1 | 36.8 |
| 10 | 96 | 112 | 50 | 9:1 | 38.8 |
| 11 | 97 | 113 | 50 | 9:1 | 44.3 |
| 12 | 97 | 114 | 50 | 9:1 | 45.8 |
| 13 | 99 | 116 | 50 | 9:1 | 45.6 |
| 14 | 99 | 119 | 50 | 9:1 | 45.9 |
| 15 | 100 | 120 | 50 | 9:1 | 40.3 |
| 16 | 103 | 125 | 50 | 9:1 | 45.6 |

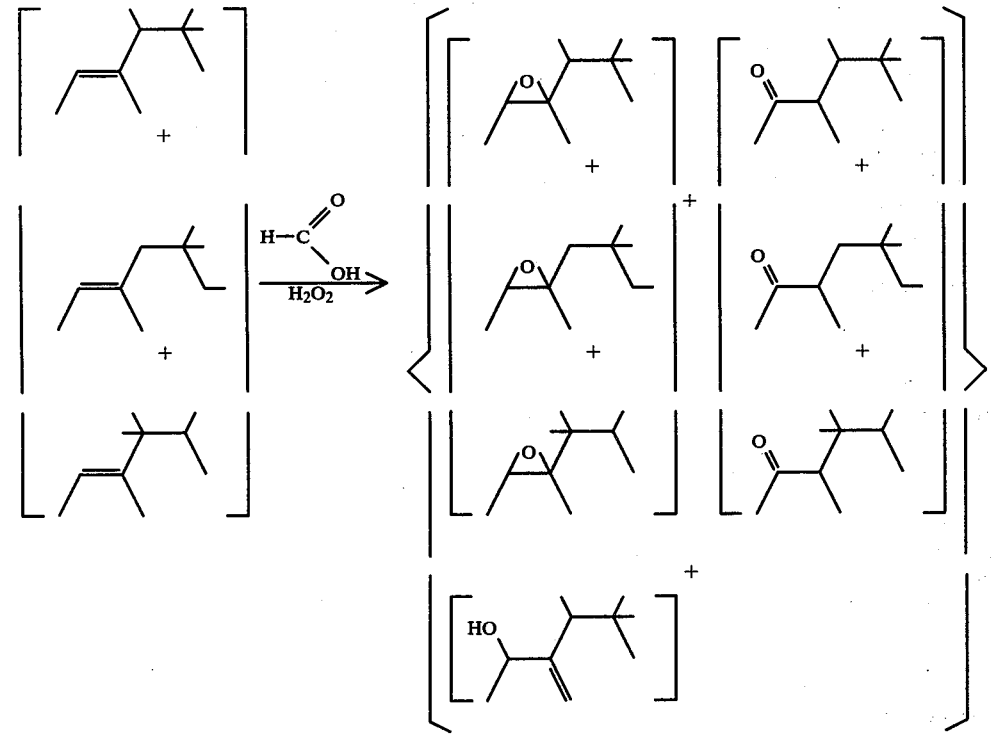

-continued

| Fraction Number | Vapor Temp. (°C.) | Liquid Temp. (°C.) | Pressure mm/Hg. | Reflux Ratio | Weight of Fraction (grams) |
| --- | --- | --- | --- | --- | --- |
| 17 | 104 | 134 | 50 | 9:1 | 50.5 |
| 18 | 107 | 140 | 50 | 9:1 | 39.6 |
| 19 | 86 | 141 | 10 | 9:1 | 38.3 |
| 20 | 150 | 152 | 10 | 9:1 | 19.2 |

Fractions 6–15 (boiling range 93°–100° C. vapor temperature; 109°–120° C. liquid temperature and 50 mm/Hg pressure) is bulked and evaluated from an organoleptic standpoint. Fractions 6–15 has a fruity, eucalyptus and hay-like aroma.

FIG. 5 is the GLC profile of the reaction product prior to distillation. FIG. 5 is described in detail in the section entitled "Detailed Description of the Drawings", supra.

FIG. 6 is the NMR spectrum for Peaks 31, 32 and 33 of FIG. 5 containing the compounds having the structures:

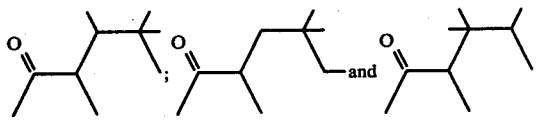

FIG. 7 is the IR spectrum for Peaks 31, 32 and 33 of FIG. 5 containing the compounds having the structures:

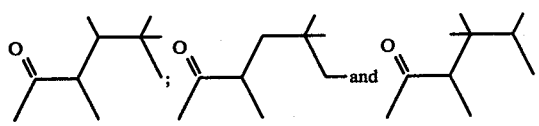

FIG. 8 is the NMR spectrum for Peaks 21, 22 and 23 of FIG. 5 containing epoxy diisoamylenes.

FIG. 9 is the infra-red spectrum for Peaks 21, 22 and 23 of FIG. 5 containing epoxy diisoamylenes.

EXAMPLE II

Preparation of Diketone Intermediate

Reaction:

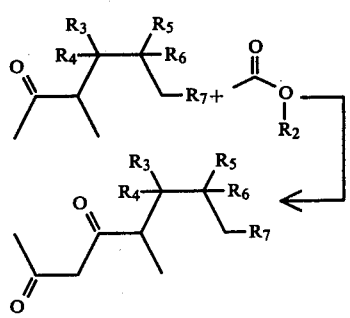

(wherein $R_2$ represents ethyl; and wherein $R_3$, $R_4$, $R_5$, $R_6$ and $R_7$ represent hydrogen or methyl with the provisos that:

(i) the sum total of the carbon atoms in $R_3$, $R_4$, $R_5$, $R_6$, and $R_7$ is three;

(ii) when $R_7$ is methyl, then $R_5$ and $R_6$ are both methyl; and (iii) when either $R_3$ or $R_4$ is methyl, then $R_7$ is hydrogen).

Into a 12 liter reaction vessel equipped with thermometer, reflux condenser, heating mantle and Bidwell trap and nitrogen blanket apparatus is placed 3595 grams (40.8 moles) of ethyl acetate and 826 grams (15.3 moles) of sodium methoxide. The resulting mixture exotherms 233° C. The reaction mass is heated to 67° C. and while maintaining the reaction mass at 67°–77° C. over a period of 1.5 hours, a mixture of ketones defined according to the structures:

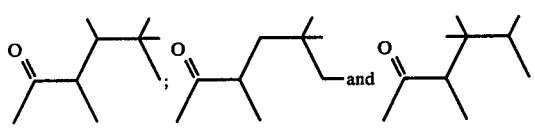

(fractions 13–15 of the distillation product of the reaction product of Example I, boiling range 97°–99° C., vapor temperature at 50 mm/Hg pressure) is added to the reaction mass. During the addition of the mixture of ketones, 60 ml of ethyl alcohol is stripped off in the Bidwell trap. The reaction mass is then stirred for an additional 11 hours at 77°–79° C. (refluxing), removing 280 ml additional ethyl alcohol.

The reaction mass is cooled and 200 ml ethyl acetate and 274 grams of sodium methoxide is added thereto.

The reaction mass is then refluxed at 78°–79° C. for an additional 8 hours during which time 180 ml of ethyl alcohol is removed therefrom.

The reaction is then quenched with 17% aqueous hydrochloric acid (3.75 liters). The reaction mass is then transferred to a separatory funnel and the aqueous phase is removed. The organic phase is washed with three two-liter portions of saturated sodium chloride (pH then in the range of 5–6). The aqueous phase is extracted with 500 ml toluene. The toluene extract is combined with the organic phase and the solvent is stripped. The resulting reaction mass is then distilled on a 1' Goodloe column yielding the following fractions:

| Fraction Number | Vapor Temp. (°C.) | Liquid Temp. (°C.) | Pressure mm/Hg. | Reflux Ratio | Weight of Fraction (grams) |
| --- | --- | --- | --- | --- | --- |
| 1 | 80/55 | 92/94 | 3.0/2.8 | 4:1 | 100 |
| 2 | 51 | 98 | 2.9 | 4:1 | 97 |
| 3 | 68 | 100 | 3.0 | 4:1 | 95 |
| 4 | 83 | 106 | 3.0 | 4:1 | 102 |
| 5 | 75/90 | 105/89 | 2.8/3.2 | 4:1/4:5 | 98 |
| 6 | 80 | 110 | 3.0 | 9:1 | 30 |
| 7 | 88 | 125 | 3.0 | 2:0/2:1 | 222 |
| 8 | 111 | 145 | 3.0 | 2:1 | 189 |
| 9 | 123 | 168 | 3.0 | 2:1 | 85 |
| 10 | 134 | 220 | 3.0 | 2:1 | 50 |

FIG. 10 is the GLC profile for fraction 5 of the foregoing distillation.

FIG. 11 is the GLC profile for fraction 6 of the foregoing distillation.

FIG. 12 is the GLC profile for fraction 7 of the foregoing distillation.

NMR and IR mass spectral analysis yield the information that fractions 5, 6 and 7 contain the compounds having the following structures:

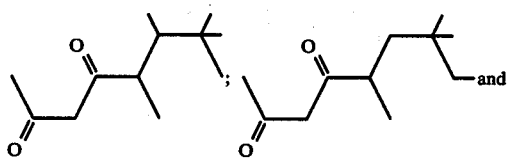

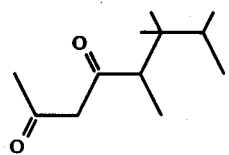

The NMR assignments are as follows:
Solvent: CFCl₃; Field Strength: 100 MHz

| Assignment | Interpretation |
|---|---|
| δ0.75–1.3 | m, 17H; 0.85(d); 0.92(s); 1.05(d) |
| δ1.96 | s, 3H; $\left(\begin{array}{c}\phantom{H_3C}\overset{\displaystyle O-H}{\underset{\displaystyle \phantom{x}}{C}}\\ H_3C\end{array}\right)$ |
| δ5.32 | s, 1H; $\left(\begin{array}{c}C=C\\ |\\ H\end{array}\right)$ |

EXAMPLE III

Preparation of Mixture of Branched C₁₃-alk-1-en-5-ones

Reactions:

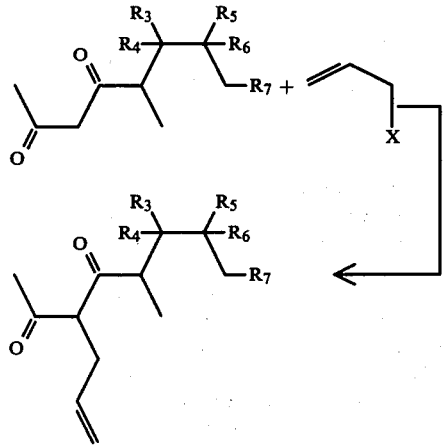

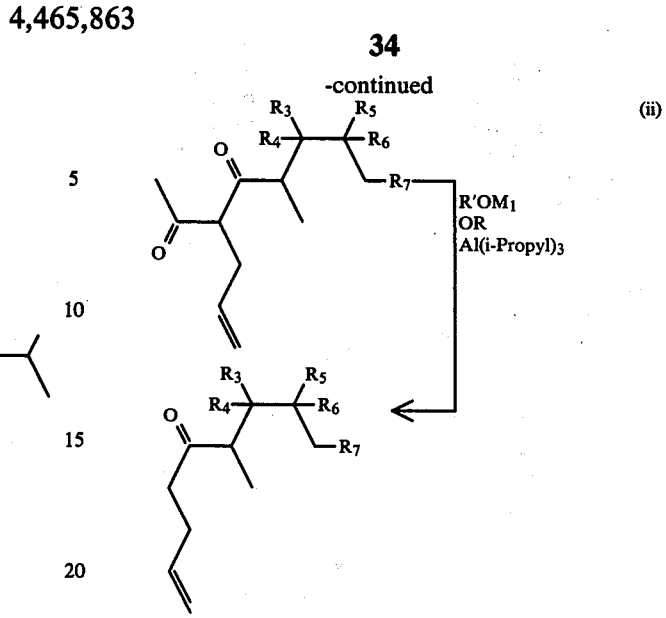

(wherein X represents iodo; and wherein R₂ represents ethyl; and wherein R₃, R₄, R₅, R₆ and R₇ represent hydrogen or methyl with the provisos that:
(i) the sum total of carbon atoms in R₃, R₄, R₅, R₆ and R₇ is three;
(ii) when R₇ is methyl, then R₅ and R₆ are both methyl; and
(iii) when either R₃ or R₄ is methyl, then R₇ is hydrogen).

Into a 1,000 ml reaction flask equipped with stirrer, condenser, thermometer, condenser, "Y" tube, addition funnel with subsurface tube, nitrogen gas blanket apparatus and gas bubbler is placed 300 ml (3 moles) of ethyl acetate; 54 grams (1 mole) of sodium methoxide; 15 grams (0.1 mole) of sodium iodide; and 198 grams of bulked fractions 5, 6 and 7 (1 mole) of the distillation product of the reaction product of Example II containing the compounds having the structures:

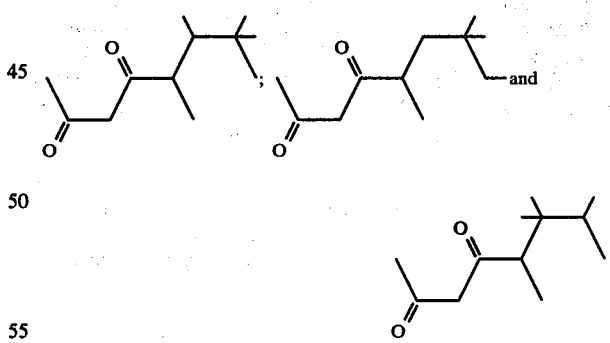

The resulting mixture exotherms to 70° C. and is then cooled to 30° C. While maintaining the reaction mass at 29°–30° C. over a period of 20 minutes, 164 ml (2 moles) of allyl chloride is added to the reaction mass. The reaction mass is then maintained at 28°–29° C. for a period of 1 hour and then heated to 60° C. and maintained at that temperature for a period of 2 hours. At the end of the 2 hour period, an additional mole of allyl chloride is added to the reaction mass. The reaction mass is then stirred for a period of 2 hours at 60° C.

The reaction mass is then transferred to a separatory funnel, fitted with a mechanical stirrer and a solution containing 1 liter of 50% sodium hydroxide, 500 ml methyl alcohol and 500 ml water at 55° C. is added slowly in three portions to the reaction mass. The reaction mass is then allowed to cool and an additional portion of the alcoholic sodium hydroxide is added. The reaction mass is then stirred for a period of 2 hours and then cooled to room temperature.

The reaction mass is then washed with an equal volume of water and then acidified to a pH of 6 with glacial acetic acid. The reaction mass is then washed once again with water and distilled on a 12"×1" Goodloe column yielding the following feactions:

| Fraction Number | Vapor Temp. (°C.) | Liquid Temp (°C.) | Pressure mm/Hg | Reflux Ratio | Weight of Fraction (grams) |
|---|---|---|---|---|---|
| 1 | 45/72 | 76/113 | 2.0/2.0 | 3:1 | 11.1 |
| 2 | 72 | 115 | 2.0 | 3:1 | 19.4 |
| 3 | 74 | 114 | 2.0 | 3:1 | 16.8 |
| 4 | 73 | 115 | 1.8 | 3:1 | 20.0 |
| 5 | 73 | 120 | 1.9 | 3:1 | 21.7 |
| 6 | 73 | 128 | 1.9 | 3:1 | 20.4 |
| 7 | 73 | 140 | 1.9 | 3:1 | 18.6 |
| 8 | 93 | 230 | 1.9 | 3:1 | 15.7 |

The resulting product as confirmed by NMR, IR and mass spectral analysis contains the compounds having the structures:

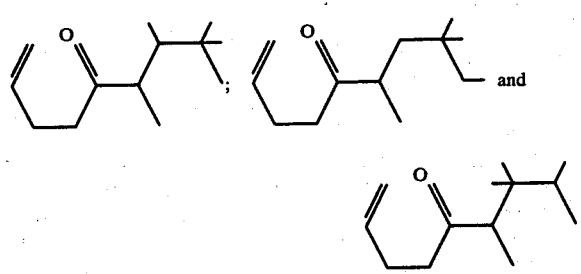

FIG. 13 is the GLC profile for the crude reaction product subsequent to caustic treatment but just prior to distillation (conditions: 6'×0.25" 12% SF-96 column programmed at 80°-220° C. at 16° C. per minute).

FIG. 14 is the GLC profile for bulked fractions 3-6 of the foregoing distillation (conditions: 6'×0.25" 12% SF-96 column programmed at 80°-220° C. at 16° C. per minute).

FIG. 15 is the NMR spectrum for bulked fractions 3-6 of the foregoing distillation product (conditions: CFCl$_3$ solvent and 100 MHz field strength).

The NMR assignments for the foregoing spectrum are as follows:

| Assignment | Interpretation |
|---|---|
| δ0.75–1.18 | m, 7(p); (s, 0.95, 9p, t-butyl) |
| δ1.6–1.78 | m, 1H |
| δ2.18–2.8 | m, 5H |
| δ21.78–5.08 | m, $\left(\begin{array}{c}\text{C}=\text{C}\begin{array}{c}\diagup\text{H}\\\diagdown\text{H}\end{array}\end{array}\right)$ |
| δ5.55–5.8 | m, 1H, $\left(\begin{array}{c}\text{H}\\\diagdown\text{C}=\text{C}\end{array}\right)$ |

FIG. 16 is the infra-red spectrum for fraction 3 of the foregoing distillation. This infra-red spectrum has a characteristic peak at 1710 cm$^{-1}$ which represents carbonyl (crystal:neat potassium bromide).

EXAMPLE IV

A base perfume composition of the "chypre" type was prepared by admixing the following ingredients:

| Ingredients | Parts by Weight |
|---|---|
| Synthetic jasmin | 150 |
| Vetiveryl acetate | 60 |
| Synthetic rose of may | 10 |
| Synthetic bulgarian rose | 50 |
| Synthetic bergamot | 150 |
| Synthetic lemon | 50 |
| Angelica roots oil 10%* | 20 |
| Alpha-isomethyl-ionone | 80 |
| Cyclopentadecanolide 10%* | 50 |
| Muscone 10%* | 50 |
| Gamma-undecalactone 10%* | 50 |
| Undecylenic aldehyde 10%* | 50 |
| Absolute oak moss 50%* | 50 |
| Dodecanal 10%* | 10 |
| Synthetic civet | 50 |
| Ylang extra | 20 |
| Sandalwood oil Mysore | 20 |
| Musk ketone | 20 |
| 1,1-dimethyl-4-acetyl-6-ter-butylindane | 10 |
| Synthetic lily of the valley | 50 |
| | 1000 |

*in diethyl phthalate

By adding to 95 grams of the above indicated base, 5 grams of a 10% solution in diethyl phthalate of bulked fractions 3-6 containing the compounds having the structures:

produced according to Example III, a novel composition was obtained. This composition possessed an original, harmonious tonality which proved to be distinctly more sophisticated than that shown by the base composition. Moreover, it possessed a green, herbal and lifting note which matches particularly well to the base odoriferous character. More specifically, it adds to the fragrance of galbanum-like, fruity, pineapple-like, woody, ionone-like, bark-like, green (intense), oily sweet aroma with floral undertones. The overall fragrance can be described as:

"chypre fragrance with strong green, galbanum-like, fruity, pineapple-like, woody, ionone-like, bark-like and oily sweet nuance with floral undertones".

EXAMPLE V

A base perfume composition for after-shave lotion was prepared by admixing the following ingredients:

| Ingredient | Parts by Weight |
|---|---|
| Synthetic bergamot | 120 |
| p-ter-butyl-cyclohexanone | 100 |
| Cedryl acetate | 100 |
| Methyl-octylacetaldehyde 10%* | 80 |
| Synthetic jasmin | 60 |
| Lemon oil | 60 |
| Florida oragne oil | 50 |
| "Mousse d'arbre" concrete 50%* | 50 |
| Absolute lavandin oil | 40 |
| Clove oil Madagascar | 40 |
| Trimethylcyclododecatriene epoxide | 40 |
| Synthetic neroli | 40 |
| Undecanal 10%* | 20 |
| Styrallyl acetate | 20 |
| Patchouli oil | 20 |
| Isocamphyl cyclohexanol | 20 |
| α-isomethyl-ionone | 20 |
| Dimethyl-cyclohexene-carbaldehyde | 20 |
| | 900 |

*in diethyl phthalate

By adding to 90 grams of the above base composition, 10 grams of a 1% in diethyl phthalate solution of a mixture of ketones defined according to the structures:

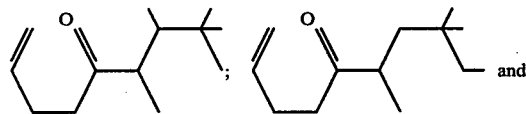

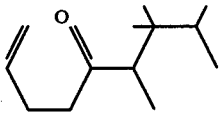

produced according to the process of Example III (bulked fractions 3–6), a novel composition was obtained. This composition possessed, when compared to the base composition, a strong galbanum-like, fruity, pineapple-like, woody, ionone-like, bark-like, green and oily-sweet aroma profile with floral undertones. The organoleptic character of the overall composition can be described as:

"herbal aroma with galbanum-like, fruity, pineapple-like, woody, ionone-like, bark-like and oily sweet nuances with floral undertones".

EXAMPLE VI

A base perfume composition for "eau-de-toilette" was prepared by admixing the following ingredients:

| Ingredient | Parts by Weight |
|---|---|
| Patchouli oil | 30 |
| Vetiveryl acetate | 50 |
| Synthetic jasmin oil | 50 |
| Synthetic rose oil | 100 |
| Galbanum oil | 20 |
| Synthetic bergamot | 80 |
| Angelica roots oil 10%* | 20 |
| alpha-isomethyl-ionone | 100 |
| Hydroxy-citronellal | 80 |
| Cyclopentadecanolide 10%* | 50 |
| gamma-undecalactone 10%* | 20 |
| Undecylenic aldehyde 10%* | 70 |
| Methyl-nonylaldehyde 10%* | 10 |
| Dodecanal 1%* | 20 |
| Phenylacetaldehyde 10%* | 20 |
| beta-damascone 10%* | 20 |
| Phenyl-methyl carbinol | 20 |
| Synthetic civet | 5 |
| Ylang | 25 |
| Sandalwood oil Mysore | 20 |
| Coumarin | 20 |
| Musk ketone | 30 |
| Oak moss 50%* | 20 |
| Eugenol | 40 |
| Lemon oil | 20 |
| Diethyl phthalate | 60 |
| | 1000 |

*in diethyl phthalate

By adding to 90 grams of the above base, 10 grams of the ketone having the structure:

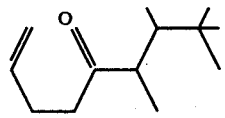

prepared according to Example III, a novel composition was obtained. This composition possessed, when compared to the base, an improved galbanum and woody aroma. The overall composition can be described as "a green aroma with intense galbanum and woody nuances".

EXAMPLE VII

A base perfume composition for toilet soaps was prepared by admixing the following ingredients:

| Ingredients | Parts by Weight |
|---|---|
| Undecylenic aldehyde 10%* | 50 |
| Methyl-nonyl aldehyde 10%* | 20 |
| Methyl 1-(1-oxo-2-pentyl-cyclopentyl)-acetate 10%* | 20 |
| Synthetic ambra 10%* | 20 |
| Ethyl methylphenylglycidate 10%* | 20 |
| Trichloro-methylphenyl carbinyl acetate | 20 |
| Coumarin | 30 |
| Heliotropine | 20 |
| 1,1-dimethyl-4-acetyl-6-ter-butyl indane | 30 |
| Acetylcedrene | 60 |
| Phenylethyl-carbinyl acetate | 10 |
| Benzyl salicylate | 30 |
| alpha-isomethyl-ionone | 60 |
| Patchouli oil | 10 |
| Hexylcinnamaldehyde | 50 |
| Phenyl-ethyl alcohol | 100 |
| Synthetic geranium | 50 |
| "Mousse d'arbre" concrete 50%* | 40 |
| Galbanum | 5 |
| Synthetic ylang | 65 |
| Cyclamen aldehyde | 40 |
| Benzyl acetate | 50 |
| Synthetic bergamot | 200 |
| | 1000 |

*in diethyl phthalate

By adding to the above base 5 percent by weight of the compound having the structure:

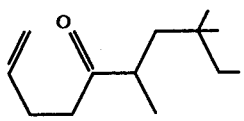

an intense galbanum, fruity, woody, bark-like aroma profile was added to this floral aroma. The overall aroma can therefore be described as "floral with intense galbanum-like, fruity and bark-like aroma nuances".

EXAMPLE VIII

A base perfume composition for a "textile refreshing" perfume was prepared by admixing the following composition:

| Ingredient | Parts by Weight |
|---|---|
| Trimethyl-hexyl acetate | 140 |
| Benzyl acetate | 80 |
| alpha-amyl-cinnamic aldehyde | 100 |
| Decanal 10%* | 10 |
| Undecanal 10% | 10 |
| Undecenal 10% | 20 |
| Dodecanal 10%* | 20 |
| Trimethyldecadienal 10%* | 20 |
| Benzyl salicylate | 80 |
| 1-hydroxymethyl-4-isopropyl-cyclohexane | 70 |
| alpha-iso-methylionone | 60 |
| Synthetic rose | 60 |
| Lilial$^R$, Givaudan & Cie SA | 50 |
| 1,1-dimethyl-4-acetyl-6-ter-butyl-indane 10%* | 50 |
| Exaltolide$^R$, Firmenich SA 10%* | 30 |
| Hydroxycitronellal | 20 |
| Rhubofix**, Firmenich SA | 20 |
| Undecalactone | 20 |
| Petitgrain oil | 10 |
| Galbanum residue | 20 |
| Linalool | 30 |
| | 9230 |

*in diethyl phthalate
**a mixture of 9-(12,13-epoxy-ethyl)-4-methyl- and 9(12,13-epoxy-ethyl)-5 methyl-tricyclo(6.2.1.0$^{2,7}$)-4,5-epoxy-undecane By adding to 92 grams of the above composition, 8 grams of the compound having the structure:

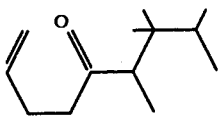

produced according to Example III, there was obtained a novel composition possessing galbanum-like, fruity, pineapple-like, ionone-like, bark-like, woody and green nuances. Thus, the overall aroma of this fragrance formulation can be described as "floral with galbanum-like, fruity, pineapple-like, woody, ionone-like and bark-like undertones".

EXAMPLE IX

Preparation of a Cosmetic Powder Composition

A cosmetic powder is prepared by mixing in a ball mill, 100 grams of talcum powder with 0.25 grams of a perfume substance as set forth in Table I below:

TABLE I

| Perfume Substance | Aroma Description |
|---|---|
| Mixture of ketones having the structures: <br><br> produced according to Example III, bulked fractions 3-6 | Galbanum-like, fruity, pineapple-like, woody, ionone-like, bark-like, green, oily sweet aroma with floral undertones. |
| Perfume composition prepared according to Example IV | Chypre fragrance with strong green, galbanum-like, fruity, pineapple-like, woody, ionone-like, bark-like and oily sweet nuance with floral undertone. |
| Perfume composition of Example V | Herbal aroma with galbanum-like, fruity, pineapple-like, woody, ionone-like, bark-like and oily sweet nuances with floral undertones. |
| Perfume composition of Example VI | A green aroma with intense galbanum and woody nuances. |
| Perfume composition of Example VII | Floral with intense galbanum-like, fruity and bark-like aroma nuances. |
| Perfume composition of Example VIII | Floral with galbanum-like, fruity, pineapple-like, woody, ionone-like and bark-like undertones. |

EXAMPLE X

Perfume Liquid Detergent

Concentrated liquid detergent (lysine salt of n-dodecylbenzene sulfonic acid as more specifically described in U.S. Pat. No. 3,948,818, issued on Apr. 6, 1976, the specification for which is incorporated herein by reference) with aroma nuances as set forth in Table I of Example IX supra are prepared containing 0.10%, 0.15%, 0.20%, 0.25%, 0.30% and 0.35% of the substances as set forth in Table I of Example IX supra. They are prepared by adding and homogeneously mixing the appropriate quantity of fragrance formulation of Table I of Example IX supra in the liquid detergents. The detergents all possess excellent aromas, the intensity increasing with greater concentration of perfume substance of Table I of Example IX.

EXAMPLE XI

Preparation of a Cologne and Handkerchief Perfume

The perfume substances as set forth in Table I of Example IX supra are incorporated into colognes at concentrations of 2.0%, 2.5%, 3.0%, 3.5%, 4.0%, 4.5% and 5.0% in 75%, 80%, 85% and 90% aqueous food grade ethanol; and into handkerchief perfumes at concentrations of 15%, 20%, 25% and 30% (in 80%, 85%, 90% and 95% aqueous food grade ethanol solutions). Distinctive and definitive aroma nuances as set forth in Table I of Example IX are imparted to the colognes and to the handkerchief perfumes at all levels indicated above.

EXAMPLE XII

Preparation of Soap Compositions

One hundred grams of soap chips (IVORY ®, produced by the Procter & Gamble Company of Cincinnati, Ohio) are mixed with 1 gram of each of the perfumery substances of Table I of Example IX, supra until homogeneous compositions are obtained. In each of the cases, the homogeneous compositions are heated under 3 atmospheres pressure at 180° C. for a period of three hours and the resulting liquids are placed into soap molds. The resulting soap cakes, on cooling, manifest excellent aromas as set forth in Table I of Example IX supra.

EXAMPLE XIII

Preparation of Solid Detergent Compositions

A detergent is prepared from the following ingredients according to Example I of Canadian Pat. No. 1,007,948, (the specification for which is incorporated herein by reference):

| Ingredient | Percent by Weight |
|---|---|
| Neodol ® 45-11 (a $C_{14}$-$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is phosphate-free detergent. A total of 100 grams of said detergent is admixed with 0.10, 0.15, 0.20 and 0.25 grams of the substances of Table I of Example IX supra. The detergent samples in each case have excellent aromas as set forth in Table I of Example IX supra.

EXAMPLE XIV

Utilizing the procedure of Example I at column 15 of U.S. Pat. No. 3,632,396, (the disclosure of which is incorporated by reference herein) a nonwoven cloth substrate useful as a drier-added fabric softening article of manufacture is prepared wherein the substrate, the substrate coating and the outer coating and the perfuming material are as follows:
1. A water dissolvable paper ("Dissolvo Paper");
2. Adogen 448 (melting point about 140° F.) as the substrate coating; and
3. An outer coating having the following formulation (melting point about 150° F.):
57% $C_{20-22}$ HAPS
22% isopropyl alcohol
20% antistatic agent
1% of one of the perfume substances of Table I of Example IX, supra.

Fabric softening compositions having aromas as set forth in Table I of Example IX are prepared which essentially consist of a substrate having a weight of about 3 grams per 100 square inches; a substrate coating having a weight of about 1.85 grams per 100 grams of substrate; and an outer coating having a weight of about 1.4 grams per 100 square inches of substrate, thereby providing a total aromatized substrate and outer coating weight ratio of about 1:1 by weight of the substrate. The aromas as set forth in Table I of Example IX are imparted in a pleasant manner to the head space in the drier on operation thereof using each of the drier-added fabric softening nonwoven fabric samples.

In the following examples, Aromox ® DMC-W and Aromox ® DMMC-W are 30% aqueous solutions of dimethyl cocoamine oxide; and Aromox ® NCMDW is a 40% aqueous solution of N-cocomorpholine oxide produced by Armac Division of ADZO of Chicago, Ill.

EXAMPLE XV

Four drops of one or more of the perfume substances as set forth in Table I of Example IX supra is added to 2 grams of Aromox ® DMC-W to produce a clear premix. The clear premix is added to 200 grams of CLOROX ® with stirring resulting in a clear, stable, single phase solution. Sufficient 1M aqueous NaOH is added to bring the pH of the mixture up to 12.8. The solution remains substantially stable at 120° F. for a period of 7 days. When the 5% aqueous sodium hypochlorite solution is used as a laundry bleach, the resulting laundry on dry-out in an atmosphere of 65% relative humidity yields substantially no characteristic "hypochlorite" odor but does have a faint, pleasant aroma as set forth in Table I of Example IX supra. Furthermore, no such characteristic "hypochlorite" aroma is retained on the hands of the individual handling such laundry in both the wet and the dry states.

EXAMPLE XVI

Aromox ® DMMC-W in various quantities is mixed with 0.1 grams of each of the substances of Table I of Example IX supra. The resulting premixes are then added to 200 grams of an aqueous 5% sodium hypochlorite solution. Sufficient 12.5M aqueous NaOH is added to bring the pH of each of the mixtures up to 13. The following results are obtained:

| Percentage Aromox ® DMMC-W | Clarity of hypochlorite solution after addition of premix |
|---|---|
| 0.23% | Clear after three days |
| 0.15% | Clear after three days |
| 0.08% | Initially slightly turbid; two phases exist after three days |

When the 5% aqueous sodium hypochlorite solutions are used as laundry bleaches, the resulting laundry batches on dry-out in an atmosphere of 65% relative humidity yields substantially no characteristic "hypochlorite" odor but do have faint, pleasant aromas as set forth in Table I of Example IX supra. Furthermore, no such characteristic "hypochlorite" aroma is retained on the hands of the individual handling such laundry batches in both the wet and the dry states.

EXAMPLE XVII

Two grams of Aromox ® DMMC-W are admixed with eight drops of each of the perfume substances of Table I of Example IX supra. Each of the premixes is then added with stirring to 200 grams of a 7% aqueous solution of lithium hypochlorite. Sufficient 3M aqueous LiOH is added to bring the pH of the solution to 13.4. The mixtures are then heated to 120° F. and maintained at that temperature with stirring for a period of one week. The resulting solution remains clear in a single phase. When used as laundry bleaches, the resulting bleached laundry batches on dry-out in an atmosphere of 50% relative humidity retain an aroma as described in Table I of Example IX whereas without the use of the substances of Table I of Example IX, the bleached laundry batches have faint characteristic disagreeable "hypochlorite" aromas.

EXAMPLE XVIII

Two grams of Aromox® DMMC-W are admixed with eight drops of each of the substances of Table I of Example IX supra. The premixes are then added with stirring to 200 grams of a mixture containing 4.5% aqueous sodium hypochlorite and 4.5% aqueous lithium hypochlorite. Sufficient 4M aqueous LiOH is added to bring the pH of the solutions to 13.4. The mixtures are then heated to 120° F. and maintained at that temperature for a period of one week. The resulting solutions remain clear in a single phase. When used as laundry bleach, the resulting bleached laundry batches on dry-out in an atmosphere of 50% relative humidity retain an aroma as set forth in Table I of Example IX supra whereas without the use of the perfume substances as set forth in Table I of Example IX supra, the bleached laundry batches have faint characteristic and disagreeable "hypochlorite" aromas.

EXAMPLE XIX

Two grams of Aromox® DMMC-W are admixed with eight drops of one of the perfume substances of Table I of Example IX supra. These premixes are then added with stirring to 200 grams of mixture containing 4% aqueous sodium hypochlorite and 4% aqueous lithium hypochlorite. Sufficient 2M aqueous NaOH is added to bring the pH of the solutions to 13.4. The mixtures are then heated to 110° F. and maintained at that temperature with stirring for a period of two weeks. The resulting solutions remain clear as a single phase when used as laundry bleaches. The resulting bleached laundry batches on dry-out in an atmosphere of 50% relative humidity retain aromas as set forth in Table I of Example IX supra whereas without the use of the perfume substances of Table I of Example IX supra, the bleached laundry batches have faint, characteristic disagreeable "hypochlorite" aromas.

EXAMPLE XX

Four drops of each of the substances of Table I of Example IX supra are added to 1.5 grams of Aromox® NCMDW to produce a clear premix. The clear premixes are added to 200 grams in each case of CLOROX® with stirring resulting in a clear single phase solution. Sufficient 1M aqueous NaOH is added to bring the pH of the mixture up to 12.8. The solution remains substantially stable at 120° F. for a period of 7 days. When the 5% aqueous sodium hypochlorite solution is used as a laundry bleach, the resulting laundry on dry-out in an atmosphere of 65% relative humidity yields substantially no characteristic hypochlorite aroma but does have a faint pleasant aroma as set forth in Table I of Example IX supra. Furthermore, no such characteristic "hypochlorite" aroma is retained on the hands of the individual handling such laundry in both the wet and the dry states.

EXAMPLE XXI

Four drops of each of the substances of Table I of Example IX supra are added to 1 gram of n-undecyl dimethyl amine oxide to produce a clear premix in each case. The clear premix is added to 200 grams of CLOROX® with stirring resulting in a clear, single phase solution. Sufficient 1M aqueous NaOH is added to bring the pH of the mixture to 12.8. The solution remains substantially stable at 120° F. for a period of 7 days. When the 5% aqueous sodium hypochlorite solution is used as a laundry bleach, the resulting laundry on dry-out in an atmosphere of 65% relative humidity yields substantially no characteristic hypochlorite odor but does have a faint pleasant odor as set forth in Table I of Example IX supra. Furthermore, no such characteristic "hypochlorite" odor is retained on the hands of the individual handling such laundry in both the wet and the dry states.

EXAMPLE XXII

Four drops of each of the substances of Table I of Example IX supra is added to 1 gram of n-dodecyl dimethyl amine oxide to produce a clear premix. The clear premix is added to 200 grams of CLOROX® with stirring resulting in a clear stable single phase solution. Sufficient 1M aqueous NaOH is added to bring the pH of the mixture up to 12.8. The solution remains substantially stable at 120° F. for a period of 7 days. When the 5% aqueous sodium hypochlorite solution is used as a laundry bleach, the resulting laundry on dry-out in an atmosphere of 65% relative humidity yields substantially no characteristic "hypochlorite" odor but does have a faint pleasant aroma as set forth in Table I of Example IX supra. Furthermore, no such characteristic "hypochlorite" aroma is retained on the hands of the individual handling such laundry in both the wet and the dry states.

EXAMPLE XXIII

One gram of n-tridecyl dimethyl amine oxide is admixed with eight drops of each of the substances of Table I of Example IX supra. Each of the premixes is then, with stirring, added to 200 grams of a 7% aqueous solution of lithium hypochlorite. Sufficient 3M aqueous LiOH is added to bring the pH of the solution to 13.4. The mixture is then heated to 120° F. and maintained at that temperature with stirring for a period of one week. The resulting solution remains clear in a single phase. When used as a laundry bleach, the resulting bleached laundry on dry-out in an atmosphere of 50% relative humidity retains an aroma as set forth in Table I of Example IX supra; whereas without the use of any of the substances of Table I of Example IX supra, the bleached laundry has a faint, characteristic, disagreeable "hypochlorite" aroma.

What is claimed is:
1. The compound defined according to the structure:

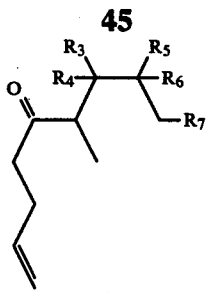
wherein $R_3$, $R_4$, $R_5$, $R_6$ and $R_7$ represent hydrogen or methyl with the provisos that:
 (i) the sum total of the carbon atoms in $R_3$, $R_4$, $R_5$, $R_6$ and $R_7$ is three;
 (ii) when $R_7$ is methyl and $R_5$ and $R_6$ are both methyl; and
 (iii) when either $R_3$ or $R_4$ is methyl and $R_7$ is hydrogen.
* * * * *